(12) United States Patent
Remillieux et al.

(10) Patent No.: US 12,130,260 B2
(45) Date of Patent: Oct. 29, 2024

(54) SYSTEMS AND METHODS FOR MODELING SUBSTANCE CHARACTERISTICS

(71) Applicants: Chevron U.S.A. Inc., San Ramon, CA (US); Triad National Security, LLC, Los Alamos, NM (US)

(72) Inventors: Marcel Remillieux, Los Alamos, NM (US); Esteban Rougier, Los Alamos, NM (US); Zhou Lei, Los Alamos, NM (US); Timothy James Ulrich, Los Alamos, NM (US); Harvey Edwin Goodman, San Ramon, CA (US)

(73) Assignee: Chevron U.S.A. Inc., San Ramon, CA (US)

( * ) Notice: Subject to any disclaimer, the term of this patent is extended or adjusted under 35 U.S.C. 154(b) by 461 days.

(21) Appl. No.: 17/602,242

(22) PCT Filed: Apr. 7, 2020

(86) PCT No.: PCT/US2020/027012
§ 371 (c)(1),
(2) Date: Oct. 7, 2021

(87) PCT Pub. No.: WO2020/210201
PCT Pub. Date: Oct. 15, 2020

(65) Prior Publication Data
US 2022/0057368 A1  Feb. 24, 2022

Related U.S. Application Data

(60) Provisional application No. 62/830,720, filed on Apr. 8, 2019.

(51) Int. Cl.
*G01N 29/12* (2006.01)
*G01N 29/44* (2006.01)
*G16C 60/00* (2019.01)

(52) U.S. Cl.
CPC ......... *G01N 29/12* (2013.01); *G01N 29/4472* (2013.01); *G16C 60/00* (2019.02); *G01N 2291/0232* (2013.01)

(58) Field of Classification Search
CPC ...... G01N 29/11; G01N 29/12; G01N 29/346; G01N 29/348; G01N 29/043;
(Continued)

(56) References Cited

U.S. PATENT DOCUMENTS 6,864,826 B1    3/2005  Stove
10,983,036 B2 *  4/2021  Roberts ............... G01N 29/227
(Continued)

OTHER PUBLICATIONS

PCT International Search Report and Written Opinion for PCT Application No. PCT/US2020/027012, mailed Jun. 18, 2020 (7 pages).

*Primary Examiner* — An H Do
(74) *Attorney, Agent, or Firm* — ESPLIN & ASSOCIATES, PC

(57) ABSTRACT

Structure information for a substance within a volume may be obtained. The structure information may characterize structural non-linearity of the substance within the volume. A structure model for the substance within the volume may be generated based on the structure information and/or other information. The structure model may simulate one or more characteristics of the substance within the volume. Presentation of information on the characteristic(s) of the substance within the volume may be effectuated based on the structure model and/or other information.

14 Claims, 23 Drawing Sheets

(58) Field of Classification Search
CPC ..... G01N 29/4472; G01N 2291/02827; G01N 2291/0289; G01N 2291/0232; G01N 2291/02491; G16C 60/00
See application file for complete search history.

(56) References Cited

U.S. PATENT DOCUMENTS

| | | |
|---|---|---|
| 11,067,711 B2 * | 7/2021 | Goodman .............. G01V 1/306 |
| 11,226,312 B1 * | 1/2022 | Remillieux ............ G01N 29/12 |
| 2005/0007527 A1 | 1/2005 | Maeda |
| 2010/0005740 A1 | 1/2010 | Lin |
| 2014/0018574 A1 | 1/2014 | Raith |
| 2016/0026591 A1 | 1/2016 | Jones |
| 2018/0017178 A1 | 1/2018 | Al-Qahtani |
| 2018/0019428 A1 | 1/2018 | Kawamura |

* cited by examiner

Normal load is a harmonic pressure signal. A sequence of harmonic signals is generated with frequencies spanning the resonance frequency of the system.

Boundary Conditions

Normal Load: $P(t) = P_0 \sin(\omega t)$

Normal load is a harmonic pressure signal. A sequence of harmonic signals is generated with frequencies spanning the resonance frequency of the system.

SYSTEMS AND METHODS FOR MODELING SUBSTANCE CHARACTERISTICS

CROSS-REFERENCE TO RELATED APPLICATION

The present application is a national stage application of International Application No. PCT/US20/27012, filed 7 Apr., 2020, which claims the benefit of U.S. Provisional Application No. 62/830,720 (the "'720 application"), entitled "SYSTEMS AND METHODS FOR MODELING SUBSTANCE CHARACTERISTICS," which was filed on Apr. 8, 2019, the entirety of which are hereby incorporated herein by reference.

FIELD

The present disclosure relates generally to the field of modeling substance characteristics based on structural non-linearity of a substance.

BACKGROUND

Simulating characteristics of a substance may be important to understanding the nature of the substance and/or to performing operations with respect to the substance. For example, a substance may include a rock structure (e.g., rock formation) to be drilled. Simulating characteristics of the rock structure may be important in identifying the type of the rock structure and/or to proper operation of a drilling tool to drill the rock formation. A model used to simulate the characteristics of the rock structure may not take into account non-linear structure of grains within the rock structure. For example, different configurations of grains within the rock structure may result in different force chains that change how the rock structure reacts to stress. A model that incorporates grain-scale interactions of the rock structure may more accurately simulate the characteristics of the rock structure.

SUMMARY

This disclosure relates to modeling substance characteristics based on structural non-linearity of a substance. Structure information for a substance within a volume may be obtained. The structure information may characterize structural non-linearity of the substance within the volume. A structure model for the substance within the volume may be generated based on the structure information and/or other information. The structure model may simulate one or more characteristics of the substance within the volume. Presentation of information on the characteristic(s) of the substance within the volume may be effectuated based on the structure model and/or other information.

A system that models substance characteristics based on structural non-linearity of a substance may include one or more electronic storage, one or more processors and/or other components. The electronic storage may store information relating to a substance within a volume, information relating to the substance, information relating to the volume, structure information, information relating to structural non-linearity of the substance within the volume, information relating to a structure model for the substance within the volume, information relating to one or more characteristics of the substance within the volume, and/or other information.

The processor(s) may be configured by machine-readable instructions. Executing the machine-readable instructions may cause the processor(s) to facilitate modeling substance characteristics based on structural non-linearity of a substance. The machine-readable instructions may include one or more computer program components. The computer program components may include one or more of a structure information component, a structure model component, a presentation component, and/or other computer program components.

The structure information component may be configured to obtain structure information for a substance within a volume and/or other information. The structure information may characterize structural non-linearity of the substance within the volume. The structure information may be determined based on analysis of the substance within the volume. For example, the structure information may be determined based on resonance frequencies of the substance within the volume. The structure information may be determined based on other analysis.

The determination of the structure information based on the resonance frequencies of the substance within the volume may include transmission of one or more acoustic waves through the substance within the volume. For example, one or more acoustic waves that travel through the substance within the volume may be received. The resonance frequencies of the substance within the volume may be determined based on the received acoustic wave(s) and/or other information.

A resonance frequency may be selected from the resonance frequencies. A resonance frequency acoustic wave may be sent through the substance within the volume multiple times. The resonance frequency acoustic wave may have the selected resonance frequency. The resonance frequency acoustic wave may have different amplitudes for individual ones of the multiple times that it is sent through the substance within the volume. Changes in the resonance frequencies of the substance within the volume as a function of the different amplitudes of the resonance frequency acoustic wave may be determined. The structural non-linearity of the substance within the volume may be determined based on the changes in the resonance frequencies of the substance within the volume as the function of the different amplitudes of the resonance frequency acoustic wave and/or other information.

In some implementations, the substance within the volume may include a rock structure, and the changes in the resonance frequencies of the substance within the volume as the function of the different amplitudes of the resonance frequency acoustic wave may indicate a change in stiffness of the rock structure.

The structure model component may be configured to generate a structure model for the substance within the volume based on the structure information and/or other information. The structure model may simulate one or more characteristics of the substance within the volume.

In some implementations, the substance within the volume may include a rock structure, and the characteristic(s) of the substance within the volume may be simulated by the structure model based on a grain-scale modeling. The characteristic(s) of the substance within the volume includes one or more of a pore pressure of the rock structure, a stress distribution within the rock structure, a force chain within the rock structure, a configuration of grains within the rock structure, a composition of the rock structure, a crack of the rock structure, a fracture of the rock structure, a fracture pattern of the rock structure, a fragmentation process of the rock structure, and/or other characteristics of the rock structure.

The presentation component may be configured to effectuate presentation of information on the characteristic(s) of the substance within the volume based on the structure model and/or other information. The information on the characteristic(s) of the substance within the volume may be presented on one or more displays.

These and other objects, features, and characteristics of the system and/or method disclosed herein, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a," "an," and "the" include plural referents unless the context clearly dictates otherwise.

DETAILED DESCRIPTION

The present disclosure relates to modeling substance characteristics based on structural non-linearity of a substance. The systems and methods of the present disclosure facilitate modeling of substance characteristics that takes into account non-linear structure of the substance. For example, the systems and methods of the present disclosure incorporate grain-scale interactions of a rock structure (e.g., rock formation, portion of rock formation to be drilled) to more accurately simulate characteristics of the rock structure. For instance, grain-scale mechanics may be linked with macroscopic linear and non-linear elasticity for purpose of determining pore pressure of the rock structure. The grain-scale mechanics of the rock structure may be dependent on force chains present within the rock structure. Proper understanding/characterization of force chains within the rock structure may enable more accurate simulation of stress behavior, pore pressure magnitude and distribution, rock formation strain field response, acoustic wave propagation, and/or other behavior of the rock structure.

Figure 1:
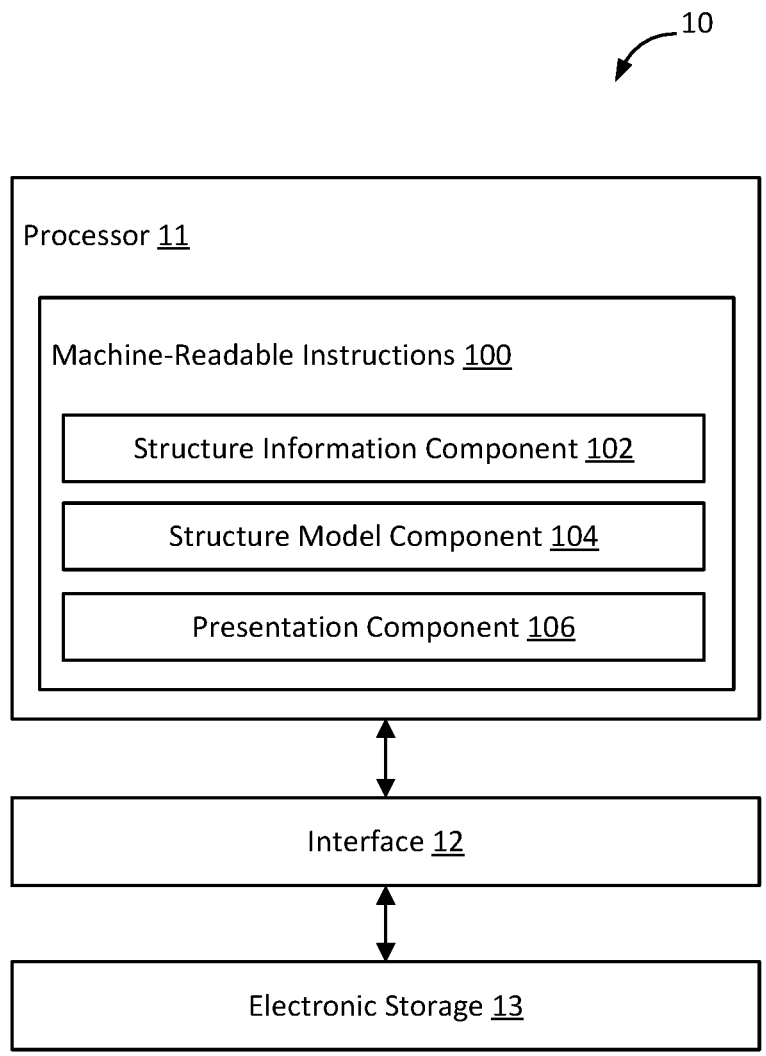
FIG. 1 illustrates an example system that models substance characteristics based on structural non-linearity of a substance.

The methods and systems of the present disclosure may be implemented by and/or in a computing system, such as a system 10 shown in FIG. 1. The system 10 may include one or more of a processor 11, an interface 12 (e.g., bus, wireless interface), an electronic storage 13, and/or other components. Structure information for a substance within a volume may be obtained by the processor 11. The structure information may characterize structural non-linearity of the substance within the volume. A structure model for the substance within the volume may be generated by the processor 11 based on the structure information and/or other information. The structure model may simulate one or more characteristics of the substance within the volume. Presentation of information on the characteristic(s) of the substance within the volume may be effectuated by the processor 11 based on the structure model and/or other information.

In some implementations, the system 10 may include one or more sensors to measure structural non-linearity of the substance within the volume. A sensor may generate one or more output signals that convey structure information for a substance within a volume. The structure information may characterize structural non-linearity of the substance within the volume.

A sensor may refer to a device that monitors (e.g., measures, ascertains, detects, estimates) one or more properties to determine structural non-linearity of the substance within the volume. A sensor may measure propert(ies) of the substance within the volume and/or propert(ies) of one or more things interacting with the substance within the volume. For example, a sensor may include a device that measures signal(s) moving through the substance within the volume (e.g., acoustic wave traveling through the substance within the volume), motion(s) of the substance within the volume (e.g., vibration of the substance within the volume), and/or other propert(ies)/reaction(s) of the substance within the volume. A sensor may include a device that generates and/or induces such signal(s), motion(s), and/or other reaction(s). For example, the system 10 may include one or more sensors and/or components described within Appendix A, Appendix B, Appendix C, and/or Appendix D of the '720 application. Other types of sensors are contemplated.

The electronic storage 13 may be configured to include electronic storage medium that electronically stores information. The electronic storage 13 may store software algorithms, information determined by the processor 11, information received remotely, and/or other information that enables the system 10 to function properly. For example, the electronic storage 13 may store information relating to a substance within a volume, information relating to the substance, information relating to the volume, structure information, information relating to structural non-linearity of the substance within the volume, information relating to a structure model for the substance within the volume, information relating to one or more characteristics of the substance within the volume, and/or other information.

The processor 11 may be configured to provide information processing capabilities in the system 10. As such, the processor 11 may comprise one or more of a digital processor, an analog processor, a digital circuit designed to process information, a central processing unit, a graphics processing unit, a microcontroller, an analog circuit designed to process information, a state machine, and/or other mechanisms for electronically processing information. The processor 11 may be configured to execute one or more machine-readable instructions 100 to facilitate modeling substance characteristics based on structural non-linearity of a substance. The machine-readable instructions 100 may include one or more computer program components. The machine-readable instructions 100 may include one or more of a structure information component 102, a structure model component 104, a presentation component 106, and/or other computer program components.

The structure information component 102 may be configured to obtain structure information for a substance within a volume and/or other information. Obtaining structure information may include one or more of accessing, acquiring, analyzing, determining, examining, identifying, loading, locating, opening, receiving, retrieving, reviewing, storing, utilizing, and/or otherwise obtaining the structure information. The structure component 102 may obtain structure information from one or more locations. For example, the structure information component 102 may obtain structure information from a storage location, such as the electronic storage 13, electronic storage of information and/or signals generated by one or more sensors and/or one or more components of sensor(s), electronic storage of a device accessible via a network, and/or other locations. The structure information component 102 may obtain structure information from one or more hardware components (e.g., sensor(s)) and/or one or more software components (e.g., software running on a computing device).

The structure information may characterize structural non-linearity of the substance within the volume. A substance may refer to physical material. A substance may be composed of a particular type of matter or a combination of different types of matter. A substance within a volume may refer to substance contained/bounded within the volume. The volume may be defined in three-dimensions. The volume may be symmetrical or asymmetrical in shape. For example, the substance may refer to a rock structure. A rock structure may refer to an arrangement of grains forming one or more pieces of rock and/or one or more portions of rock. For example, a rock structure may include a rock formation (e.g., sedimentary rock) and the substance within the volume may refer to a portion of the rock formation that is to be drilled and/or a portion of the rock formation near, adjacent, and/or below a borehole within the rock formation. Other types of substance are contemplated.

Structural non-linearity of the substance within the volume may refer to non-uniform arrangement of matter(s) making up the substance. Structural non-linearity of the substance within the volume may refer to non-linear response, reaction, and/or characteristic of the substance within the volume due to non-uniform arrangement of matter(s) making up the substance. Matter(s) making up the substance may be non-uniformly arranged in one or more directions. For example, structural non-linearity of a rock structure may refer to non-uniform arrangement of grains and/or other matter making up the rock structure. Configuration of grains within the rock structure may be non-uniform due to different sizes of grains, different shapes of grains, different orientations of grains with respect to other grains, different types of grains, inclusion of non-rock matters (e.g., fluid) within the rock structure, voids within the rock structure, and/or other non-linearity within the rock structure. Other types of structural non-linearity are contemplated.

Structural non-linearity of a rock structure may result in the presence of one or more force chains within the rock structure. A force chain may refer to a set/chain of grains within the rock structure that transmit force through the rock structure. A force chain may include a set/chain of grains within the rock structure that interact (e.g., are compressed) when force/load/stress is applied to the rock structure. Grains that are part of the force chain may form regions of high stress within the rock structure while grains that are not part of a force chain may form regions of low stress within the rock structure. For example, an acoustic wave traveling through a homogenous material may travel uniformly through the material (e.g., with equal strength across the cross section of the material). An acoustic wave traveling through a non-homogenous material may travel non-uniformly through the material (e.g., with non-equal strength across the cross section of the material). Structural non-linearity of the rock structure may result in non-uniform stress distribution through the rock structure.

The structure information may be determined based on analysis of the substance within the volume. Analysis of the substance within the volume may include examination of properties (e.g., elements, structure, attribute, quality, characteristic) of the substance within the volume and/or examination of properties of one or more things interacting with the substance within the volume. For example, the structure information may be determined based on resonance frequencies of the substance within the volume. The structure information may be determined based on other analysis, such as those described in Appendix A, Appendix B, Appendix C, and/or Appendix D of the '720 application. Non-limiting list of techniques which may be used determine structure information include dynamic acoustic elasticity measurements, time-reversal and focusing of acoustic waves, and/or following propagation of waves through the substance within the volume.

Figure 3:
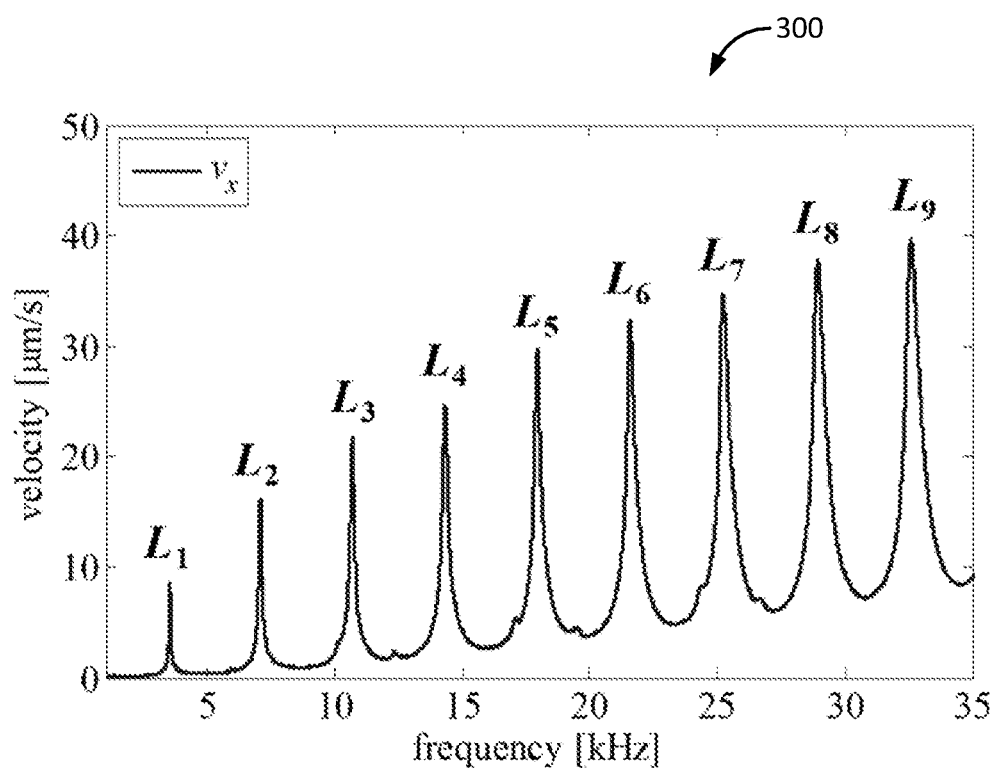
FIG. 3 illustrates an example plot of amplitude spectrum of vibration response averaged over multiple positions of sample surface.

The determination of the structure information based on the resonance frequencies of the substance within the volume may include transmission of one or more acoustic waves through the substance within the volume. An acoustic wave may include a longitudinal wave that propagates by means of adiabatic compression and decompression. An acoustic wave may include a torsional wave or a bending wave. Other types of acoustic waves are contemplated. The acoustic wave(s) may be generated and propagated through the substance within the volume. The acoustic wave(s) traveling through the substance within the volume may be received by one or more sensors to determine the resonance frequencies of the substance within the volume. FIG. 3 illustrates an example plot 300 of amplitude spectrum of vibration response averaged over multiple positions of sample surface. Individual peaks $L_\#$ within the plot 300 may correspond to a resonance frequency of the substance within the volume.

At least one of the resonance frequencies may be selected for generation of a resonance frequency acoustic wave. A resonance frequency acoustic wave may refer to an acoustic wave having the selected resonance frequency. The resonance frequency acoustic wave may be generated multiple times with different amplitudes. The resonance frequency acoustic wave may be sent through the substance within the volume multiple times. The resonance frequency acoustic wave may have different amplitudes for individual ones of the multiple times that it is sent through the substance within the volume. That is, the resonance frequency acoustic wave having different amplitudes may be sent through the substance within the volume.

If the matter(s) within the substance within the volume is uniformly arranged, the resonance frequencies of the substance within the volume may not change with different amplitudes of the resonance frequency acoustic wave. If the matter(s) within the substance within the volume is non-uniformly arranged, the resonance frequencies of the substance within the volume may change with different amplitudes of the resonance frequency acoustic wave. Non-uniform arrangement of matter(s) within the substance within the volume may result in non-linear response, reaction, and/or characteristic of the substance within the volume. For example, if grains within a rock structure is not uniformly bonded and/or there is motion of fluid within the rock structure, the resonance frequencies of the rock structure may change as a function of the amplitudes of the resonance frequent acoustic wave.

Figure 4:
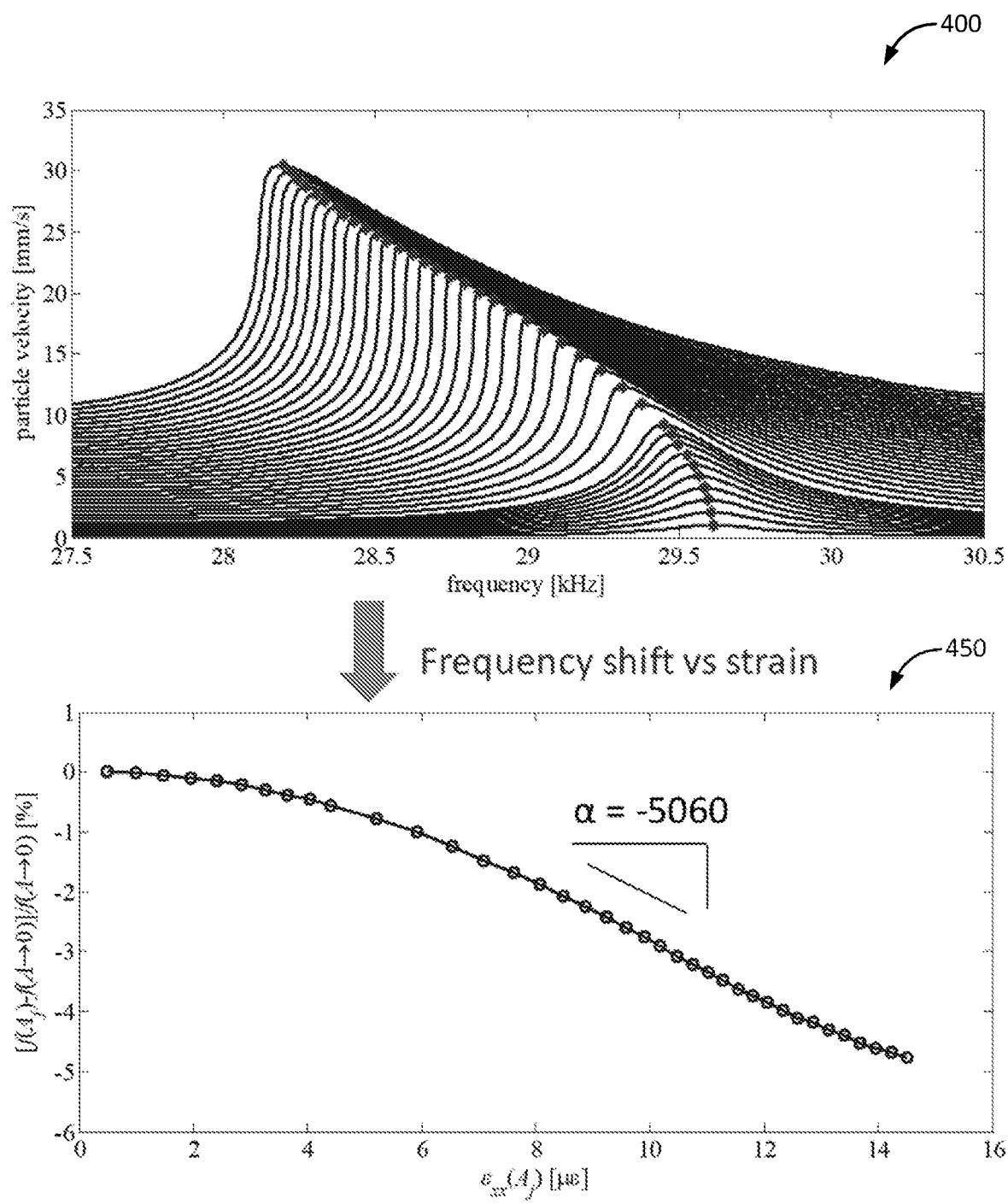
FIG. 4 illustrates an example plot showing changes in frequency as a function of particle velocity and an example plot showing relationship between frequency shift vs strain.
Figure 5:
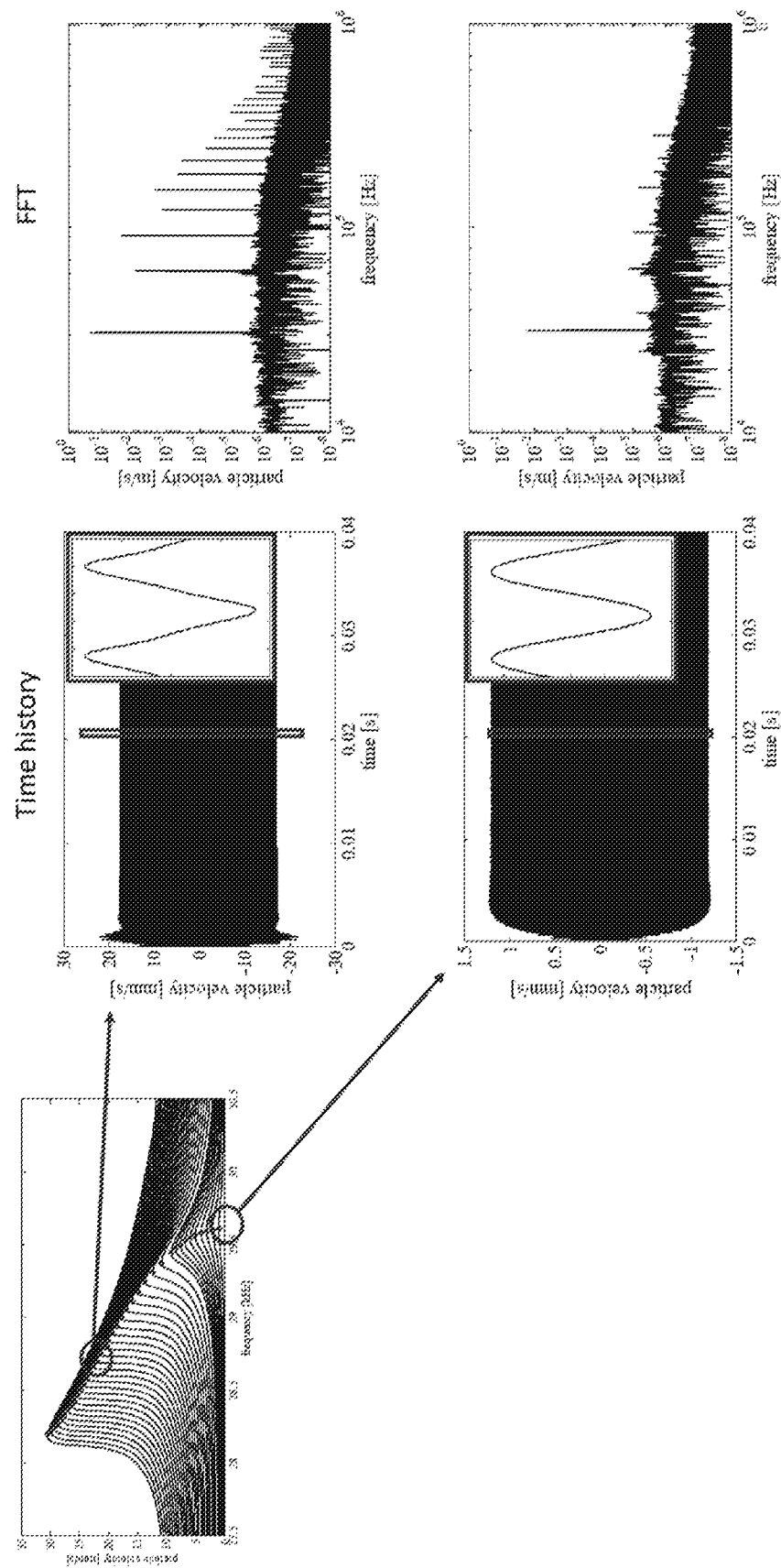
FIG. 5 illustrates an example time history and fast Fourier transform views of the plot shown in FIG. 4.

For example, FIG. 4 illustrates an example plot 400 showing changes in frequency as a function of particle velocity, and an example plot 450 showing relationship between frequency shift vs strain. The plot 400 shows the changes in frequency as a function of particle velocity changing from being linear to non-linear. FIG. 5 illustrates example time history and fast Fourier transform views of the plot 400 at two different frequencies.

The changes in resonance frequencies of the substance within the volume as a function of different amplitudes of the resonance frequency acoustic wave may be determined. The dependence of the resonance frequencies as a function of amplitude of the resonance frequency acoustic wave may be determined based on analysis of the resonance frequency acoustic waves that travel through the substance within the volume and/or based on analysis of the substance within the volume during propagation of the resonance frequency acoustic waves.

The structural non-linearity of the substance within the volume may be determined based on the changes in the resonance frequencies of the substance within the volume as the function of the different amplitudes of the resonance frequency acoustic wave and/or other information. The impact that the different amplitudes of the resonance frequency acoustic wave have on the resonance frequencies of the substance within the volume may be used to determine the non-uniform arrangement of matter(s) within the substance and/or how the non-uniform arrangement of matter(s) within the substance impacts one or more characteristics of the substance. For example, the changes in the resonance frequencies of the rock structure within the volume as the function of the different amplitudes of the resonance frequency acoustic wave may be used to determine the configuration of grains within the rock structure (e.g., the non-uniform arrangement of grains within the rock structure), the force chains within the rock structure resulting from non-uniform configuration of grains within the rock structure, and/or other characteristics of the rock structure. For instance, non-uniform distribution of grain loads may be inferred by non-linear behavior of the rock structure and/or mapped using one or more modeling techniques.

In some implementations, the changes in the resonance frequencies of the substance within the volume as the function of the different amplitudes of the resonance frequency acoustic wave may indicate one or more changes in stiffness of the substance within the volume. For example, with respect to the rock structure, force chains within the rock structure may control how load is carried different grains within the rock structure. Different stresses applied to different portions of the rock structure may change the arrangement of the grains within the rock structure. Such changes in grain configuration may not change the overall density of the rock structure but may change the force chain(s) within the rock structure. Changes in the force chain(s) within the rock structure may change the stiffness of the rock structure.

For example, application of load on the rock structure having non-uniform force chains may change the internal arrangement of grains such that the stiffness of the rock structure drops without change in the overall density of the rock structure. Such changes in the characteristics of the rock structure may impact measurements regarding the rock structure. Thus, existence of and/or changes in force chains within the rock structure may need to be considered to properly measure/model characteristics of the rock structure (e.g., change in stress as a function of depletion, change in stress as a function of pore pressure, identification of oil within the rock structure, identification of location of oil within the rock structure, identification of volume of oil within the rock structure, identification of fracture/crack).

The structure model component 104 may be configured to generate a structure model for the substance within the volume based on the structure information and/or other information. The structure model may refer to a computer-based model that is designed to simulate the substance within the volume. The structure model may simulate one or more characteristics of the substance within the volume. A characteristic of a substance may refer to a feature or a quality of the substance. A characteristic of a substance may include a static characteristic or a dynamic characteristic. For example, a characteristic of the substance simulated by the structure model may include the composition of matter(s) making up the substance. As another example, a characteristic of the substance simulated by the structure model may include how the composition of matter(s) making up the substance changes (e.g., over time, as a function of applied force amount).

In some implementations, the substance within the volume may include a rock structure, and the characteristic(s) of the substance within the volume includes one or more of a pore pressure of the rock structure, a stress distribution within the rock structure, a force chain within the rock structure, a configuration of grains within the rock structure, a composition of the rock structure, a crack of the rock structure, a fracture of the rock structure, a fracture pattern of the rock structure, a fragmentation process of the rock structure, and/or other characteristics of the rock structure.

A pore pressure may refer to pressure of fluids within pores of the rock structure. A stress destitution may refer to how stress within the rock structure may be distributed among different portions (e.g., grains) of the rock structure. A force chain within the rock structure may refer to a set/chain of grains within the rock structure that transmit force through the rock structure. A configuration of grains within the rock structure may refer to an arrangement of grains within the rock structure. A composition of the rock structure may refer to the type of matters included within the rock structure. A crack of the rock structure may refer to a line on the surface of the rock structure which has split without breaking the rock structure into separate parts. A fracture of the rock structure may refer to breaking up of the rock structure into separate parts. A fracture pattern of the rock structure may refer to an arrangement of multiple fractures within the rock structure. A fragmentation process of the rock structure may refer to series of actions/reactions within the rock structure that lead to fragmentation (breaking up) of the rock structure. The structure model may simulate one or more of the above and/or other characteristics of the rock structure statically (e.g., simulate a characteristic at a point in time) and/or dynamically (e.g., simulate a characteristic at multiple points in time, simulate a characteristic as a function of different amounts of force).

The usage of the structure information of the substance within the volume may enable component-scale modeling within the structure model. A component may refer to a part or an element of the substance within the volume. For example, the substance within the volume may include a rock structure, and the characteristic(s) of the substance within the volume may be simulated by the structure model based on a grain-scale modeling. Grain-scale modeling may enable more accurate simulation of the characteristic(s) of the rock structure by taking into account the non-uniform structure of grains within the rock structure. For example, compaction and change in porosity of a rock structure may be simulated by the structure model to more accurate estimate pore pressure of the rock structure. Grain-scale modeling of the structure model may be used in conjunction with and/or used to improve the techniques described in Appendix A, Appendix B, Appendix C, and/or Appendix D of the '720 application. Additional details regarding component-scale modeling are provided in Appendix E of the '720 application.

A model that does not provide grain-scale modeling and/or that does not take non-uniform structure of grain within the rock structure may treat the grains within the rock structure as a homogenous medium. Such a model may assume uniform change in porosity with pore pressure, even though in actuality there may be different sizes of pore and/or the non-uniform distribution of pores within the rock structure. When the rock structure includes non-uniform structure and one or more force chains, there may not be a direct link between porosity and pore pressure. For instance, grains outside the force chain(s) may not be actively supporting the load on the rock structure. A model that does not provide grain-scale modeling and/or that does not take non-uniform structure of grain within the rock structure may not properly simulate such grain-scale interactions within the rock structure. Instead, such a model may merely provide average values.

FIGS. 6-20 illustrate example views of information obtained from a structure model of a rock structure, information used to determine the structure model of the rock structure, and comparison of information obtained from the structure model of the rock structure and information obtained from experiments.

Figure 6:
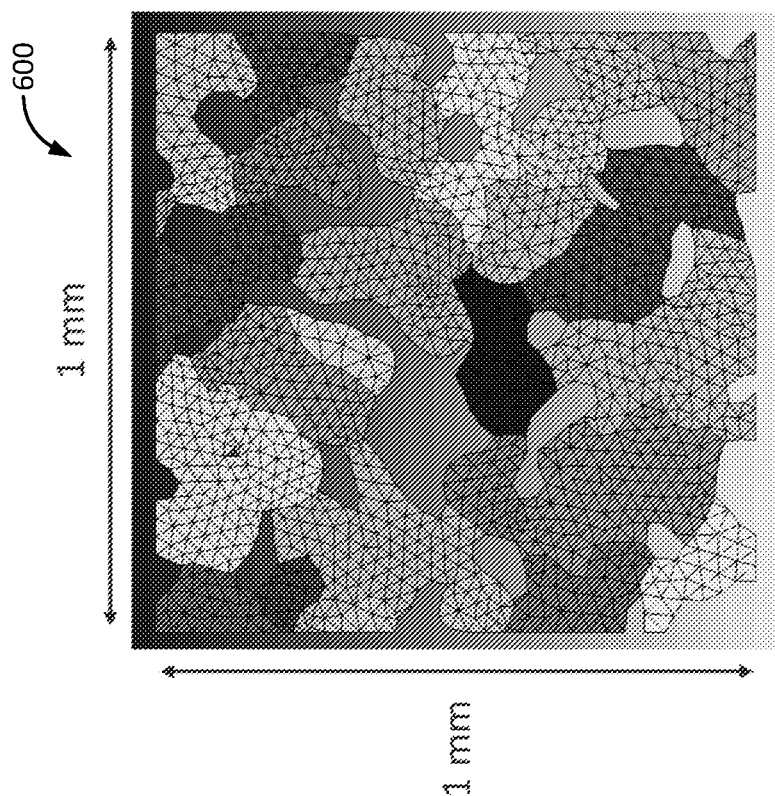
FIG. 6 illustrates an example cross-sectional view of a model of a rock structure.

FIG. 6 illustrates an example cross-sectional view 600 of a model of a rock structure. The view 600 may be generated based on the structure model for the rock structure. The view 600 may include a mesh model of a 1 mm by 1 mm portion of the rock structure. Individual grains within the view 600 may be distinguished by a single color. The grains within the mesh model may be simulated to have the properties of one or more particular types of rock (e.g., Quartz, E=97.8 GPA; v=0.07). Pore space within the rock structure may be left as voids within view 600 of the mesh model. In some implementations, the pore space within the rock structure may be modeled.

Figure 7A:
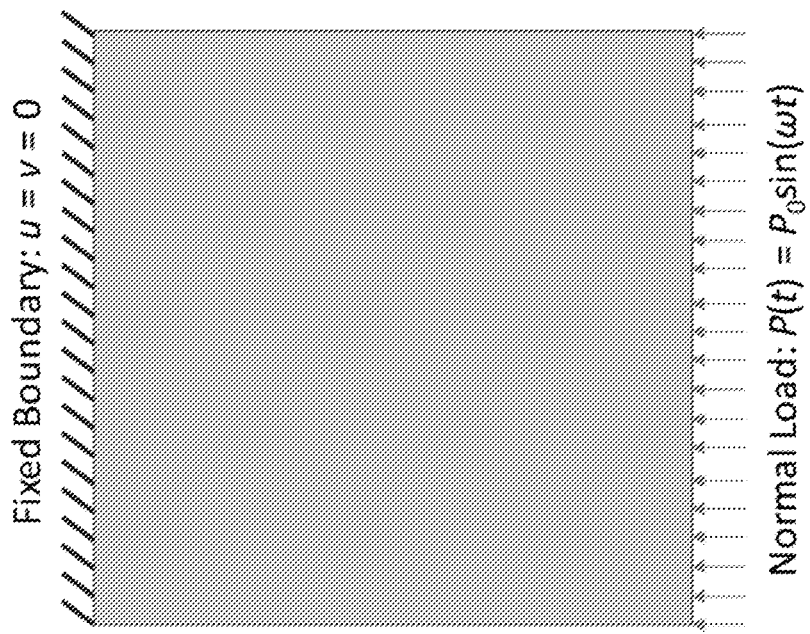
FIG. 7A illustrates example boundary conditions for modeling.
Figure 7B:
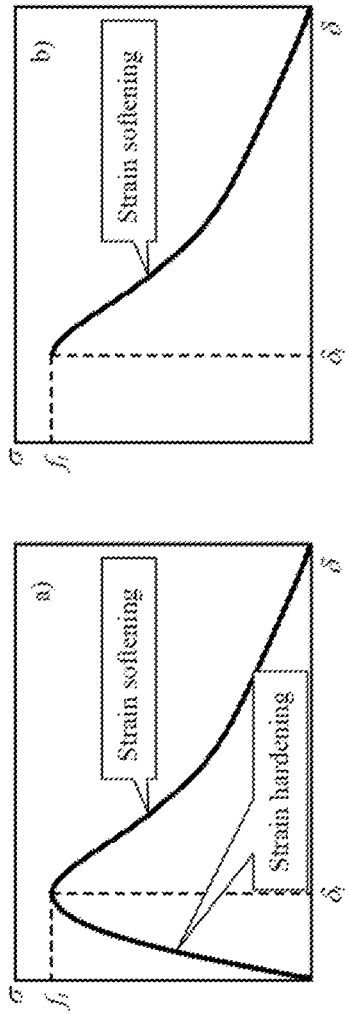
FIG. 7B illustrates example boundary conditions for modeling.
Figure 7B:
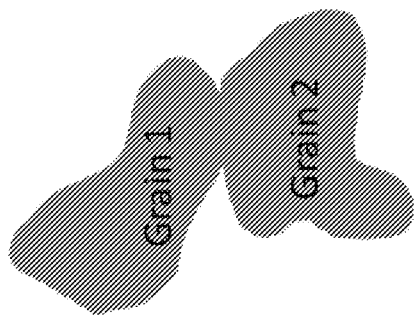
Figure 7B:
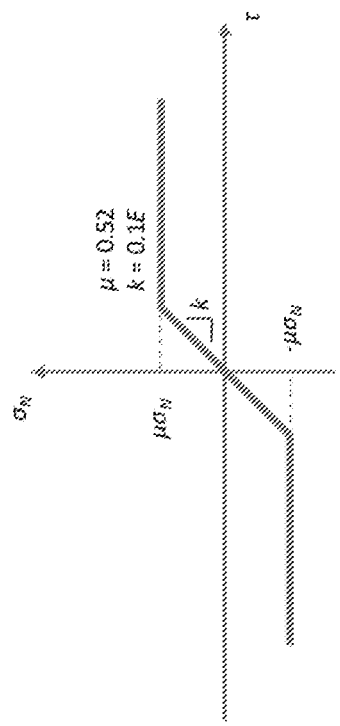

FIGS. 7A and 7B illustrate example boundary conditions for modeling. FIG. 7A illustrate example exterior boundaries and FIG. 7B illustrate example interior grain-grain boundaries.

Figure 8:
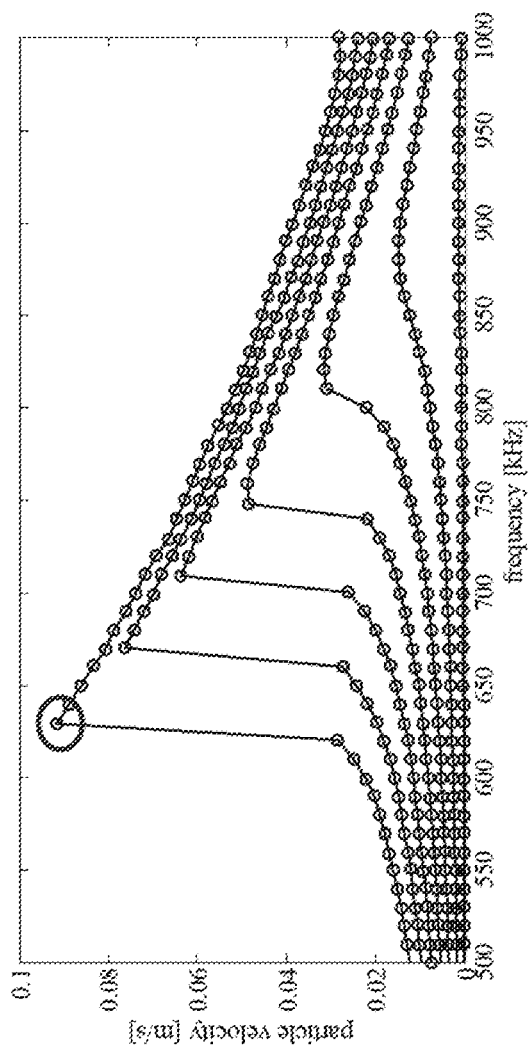
FIG. 8 illustrates example stress map and damage map for the model shown in FIG. 6.
Figure 8:
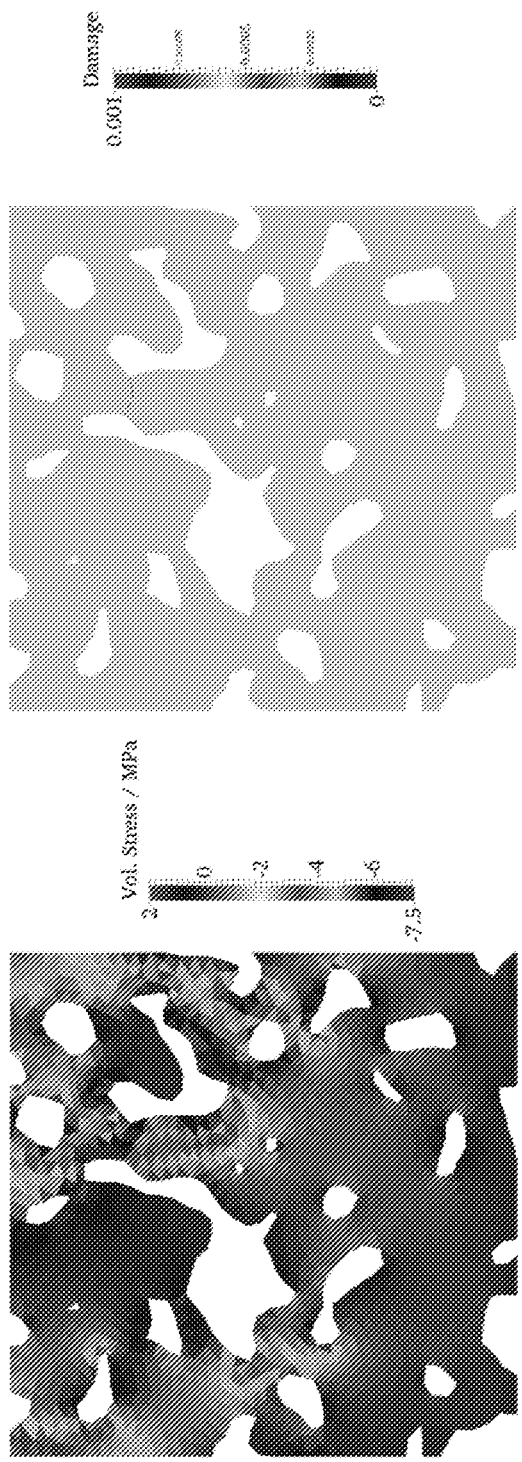

FIG. 8 illustrates example stress map and damage map for the model shown in FIG. 6. The example stress map and damage map shown in FIG. 8 may correspond to the particle velocity of about 0.09 m/s and frequency of about 630 kHz. The stress map may show the distribution of stress throughout the cross-sectional view of the model of the rock structure. Grain-scale modeling of the rock structure may enable identification of those portion(s) of the rock structure with different amounts of stress. For example, as shown in FIG. 8, narrow connections of grains may lead to areas of high stress. The points/connections in the rock structure that carry stress throughout the rock structure may result in non-linear stress changes (e.g., increases) in the rock structure.

Figure 9A:
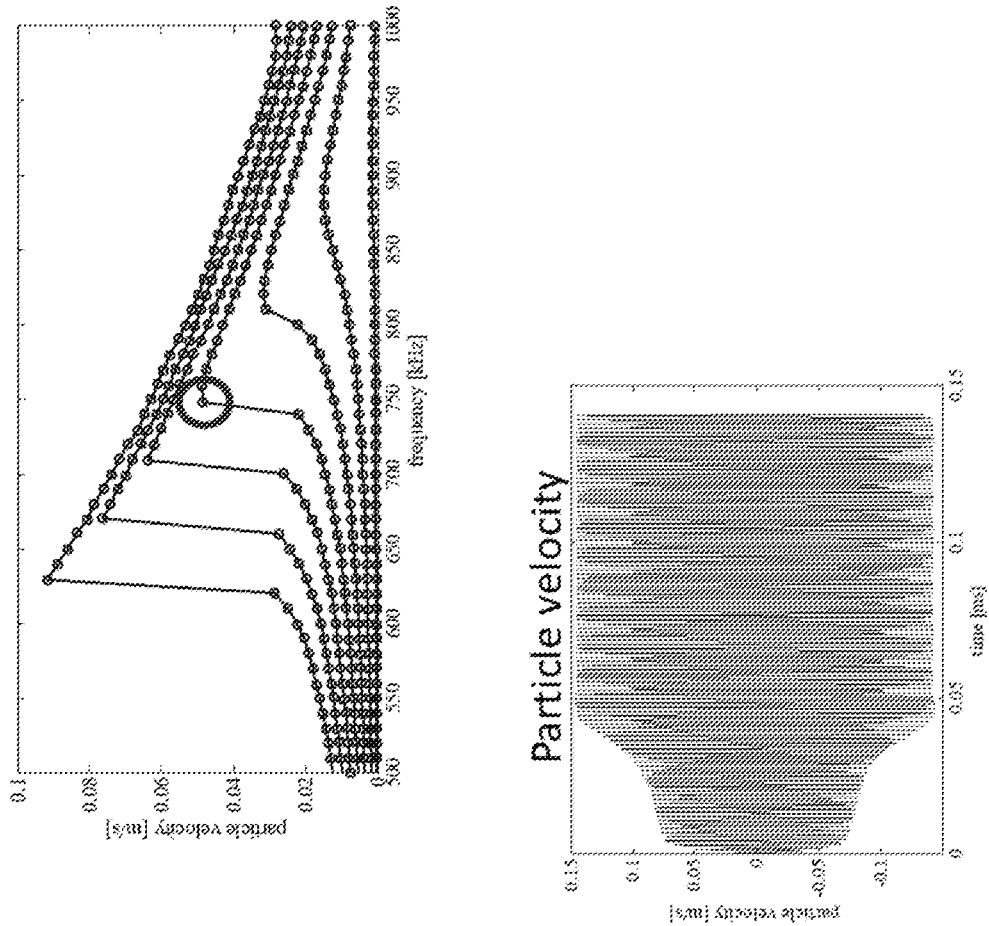
FIG. 9A illustrates an example particle velocity graph for a point within a model of a rock structure.
Figure 9A:
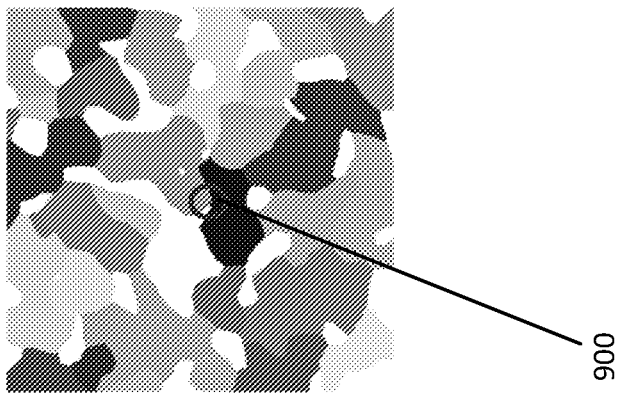
Figure 9B:
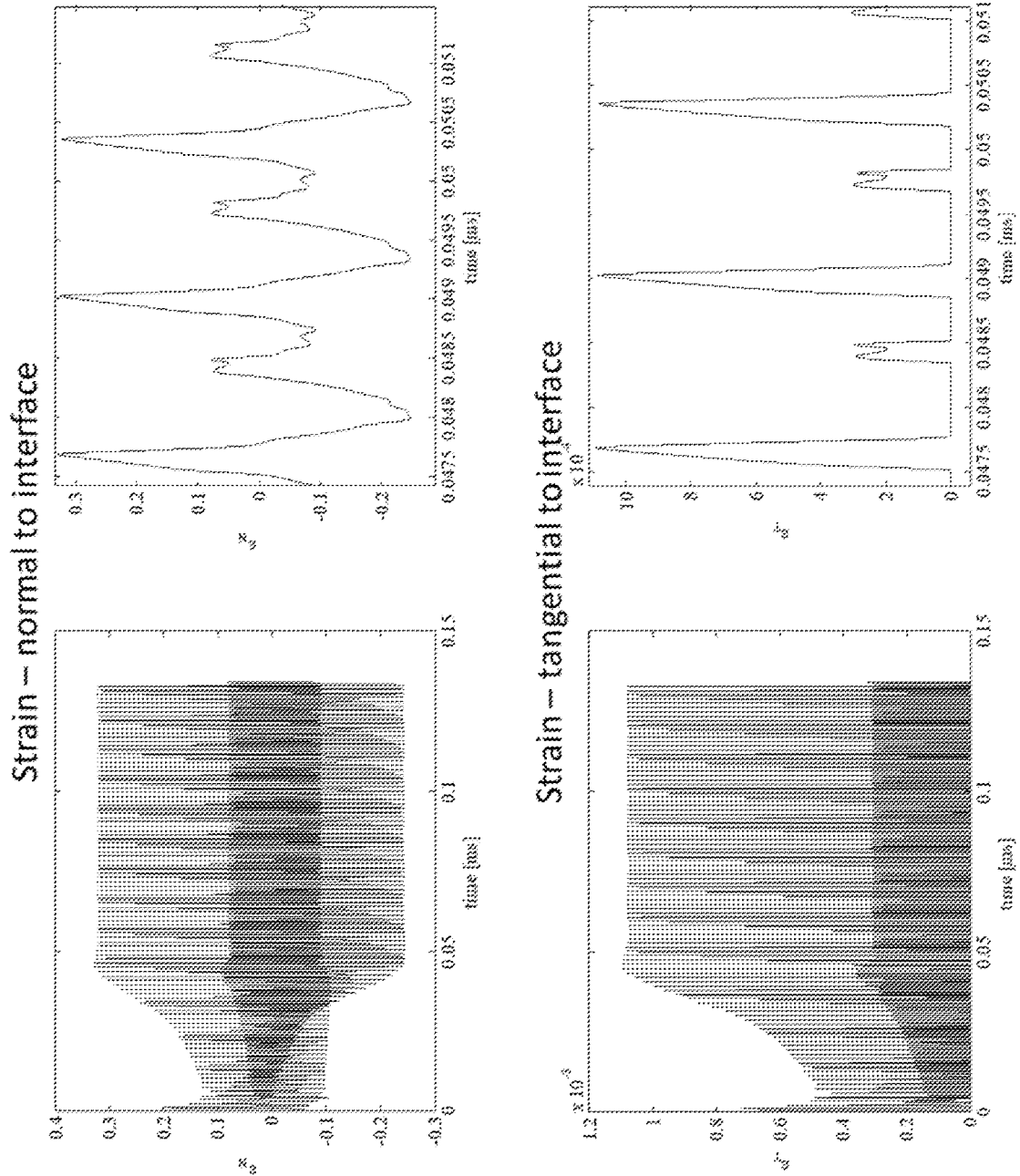
FIG. 9B illustrates example strain graphs for a point within a model of a rock structure.

FIG. 9A illustrates an example particle velocity graph for a point 900 within a model of a rock structure, and FIG. 9B illustrates example strain graphs (normal to interface, tangential to interface) for the point 900 within the model of the rock structure.

Figure 10:
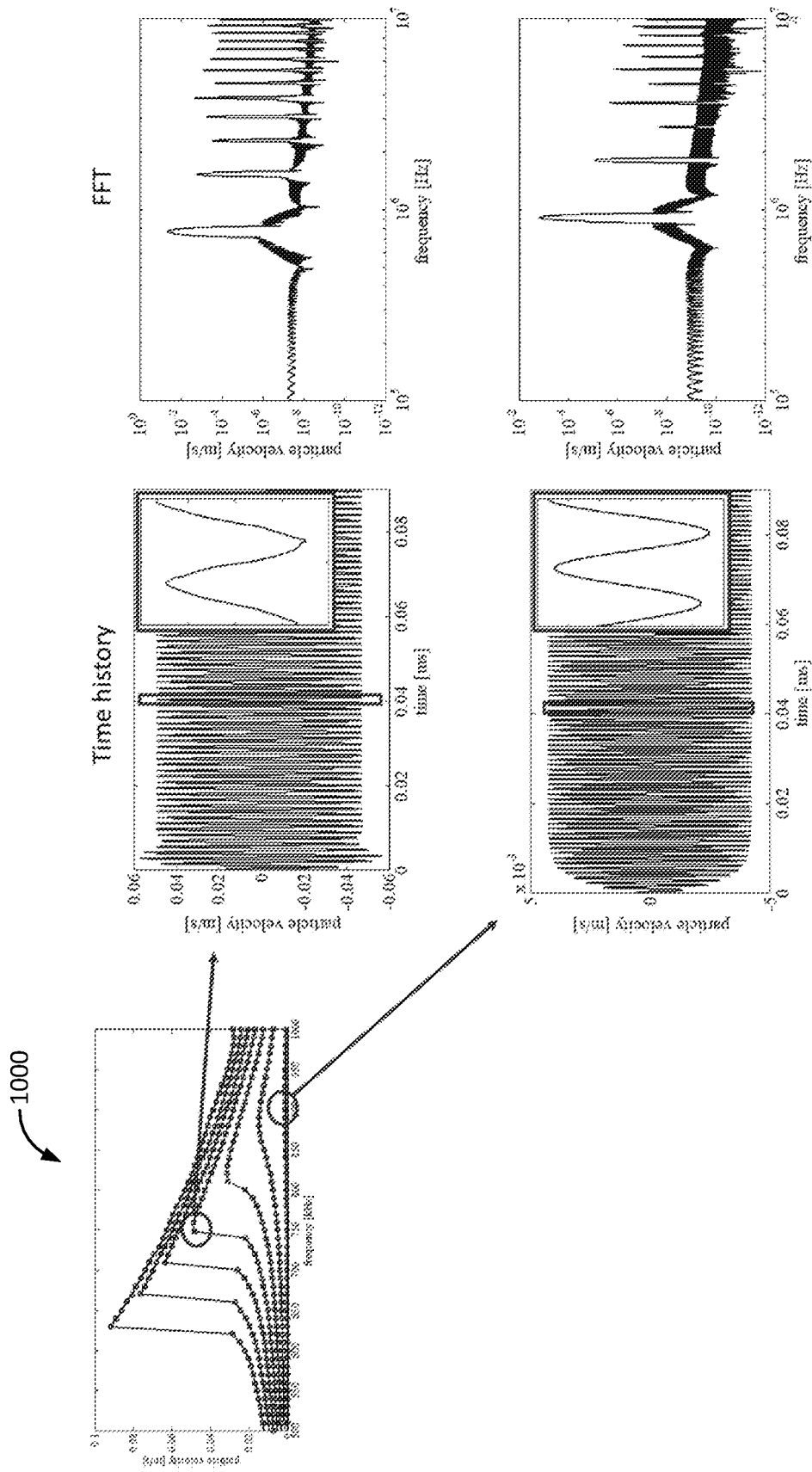
FIG. 10 illustrates example time history and fast Fourier transform views.

FIG. 10 illustrates example time history and fast Fourier transform views of a plot 1000.

Figure 11:
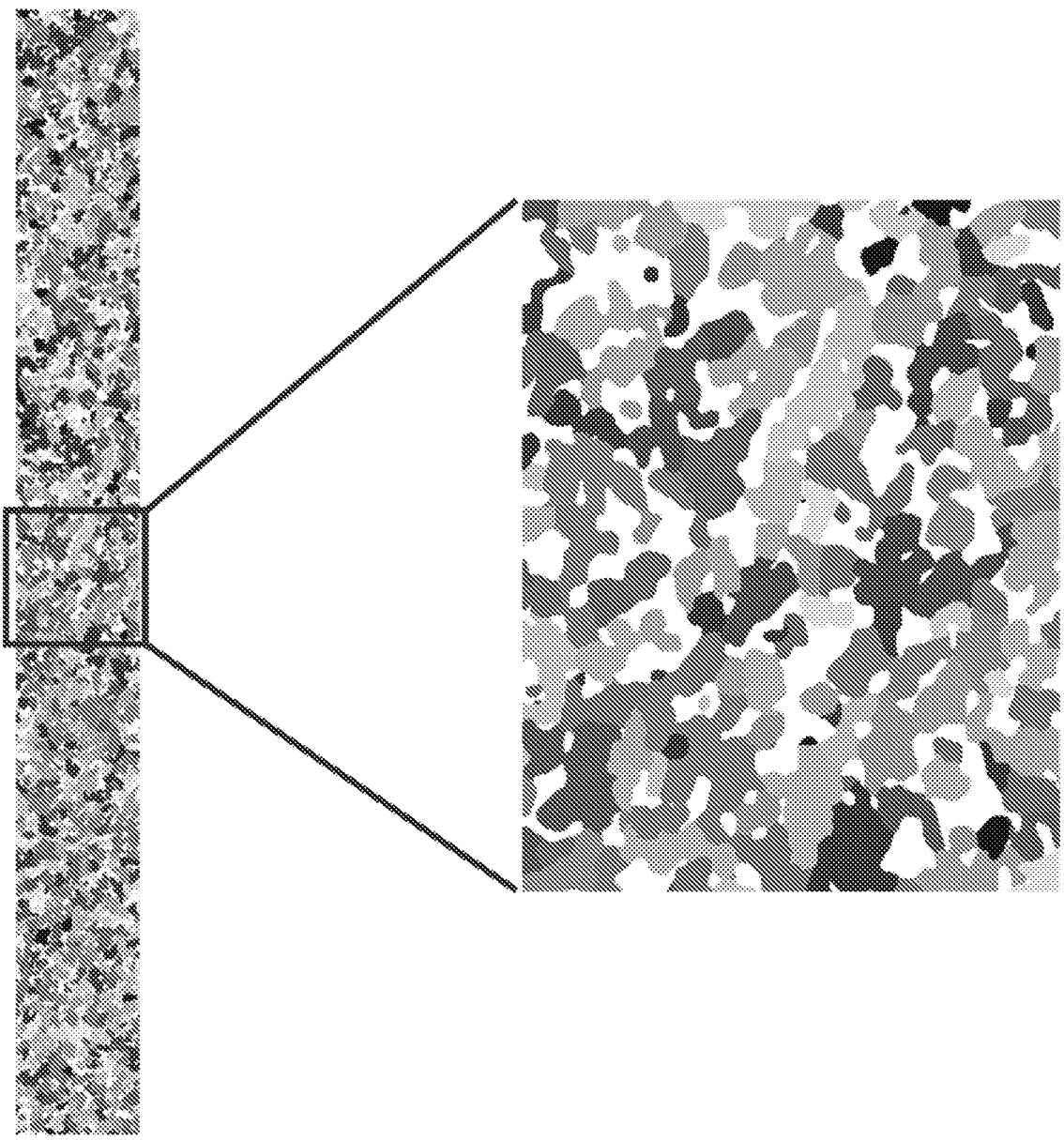
FIG. 11 illustrate an example geometry of a rock structure as modeled by a structure model of a rock structure.

FIG. 11 illustrate an example geometry of a rock structure as modeled by a structure model of a rock structure. The example geometry shown in FIG. 11 may include a view of a 2 mm by 20 mm cross section.

Figure 12:
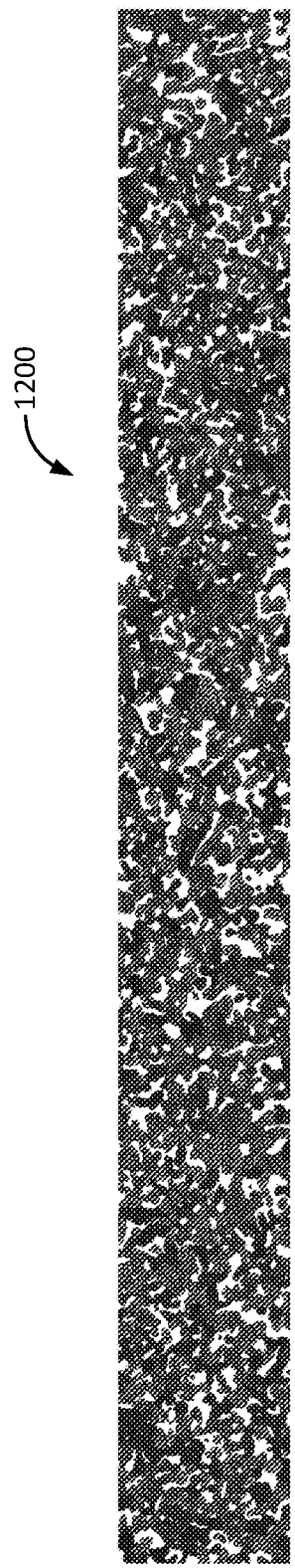
FIG. 12 illustrates an example preliminary mesh generated for a rock structure

FIG. 12 illustrate an example preliminary mesh 1200 generated for a rock structure. The preliminary mesh 1200 may be very coarse (e.g., about 30,000 elements) and a scoping study may be performed on where the resonance frequency of the first longitudinal mode is located.

Figure 13:
FIG. 13 illustrates example boundary conditions for modeling.

FIG. 13 illustrate example boundary conditions for modeling. The grains within the model may be simulated to have the properties of one or more particular types of rock (e.g., Quartz, E=97.8 GPA; v=0.07; p=2650 kg/m$^3$). Linear contact stiffness may be 20% of grain stiffness. The linear contact stiffness may be adjusted to match experimental bulk properties.

Figure 14:
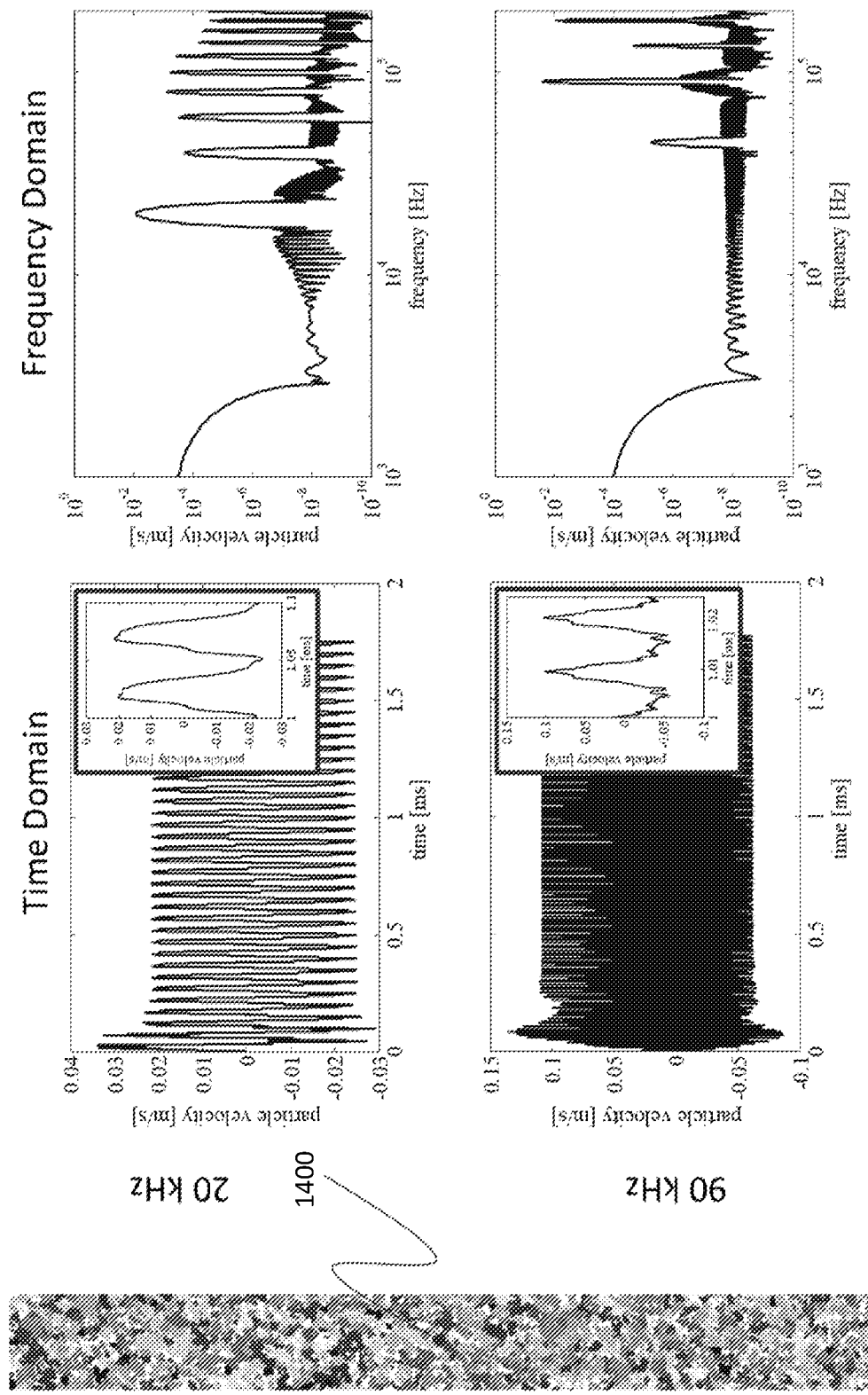
FIG. 14 illustrates example time domain and frequency domain particle velocity graphs for a point within a model of a rock structure.

FIG. 14 illustrates example time domain and frequency domain particle velocity graphs for a point 1400 within a model of a rock structure.

Figure 15A:
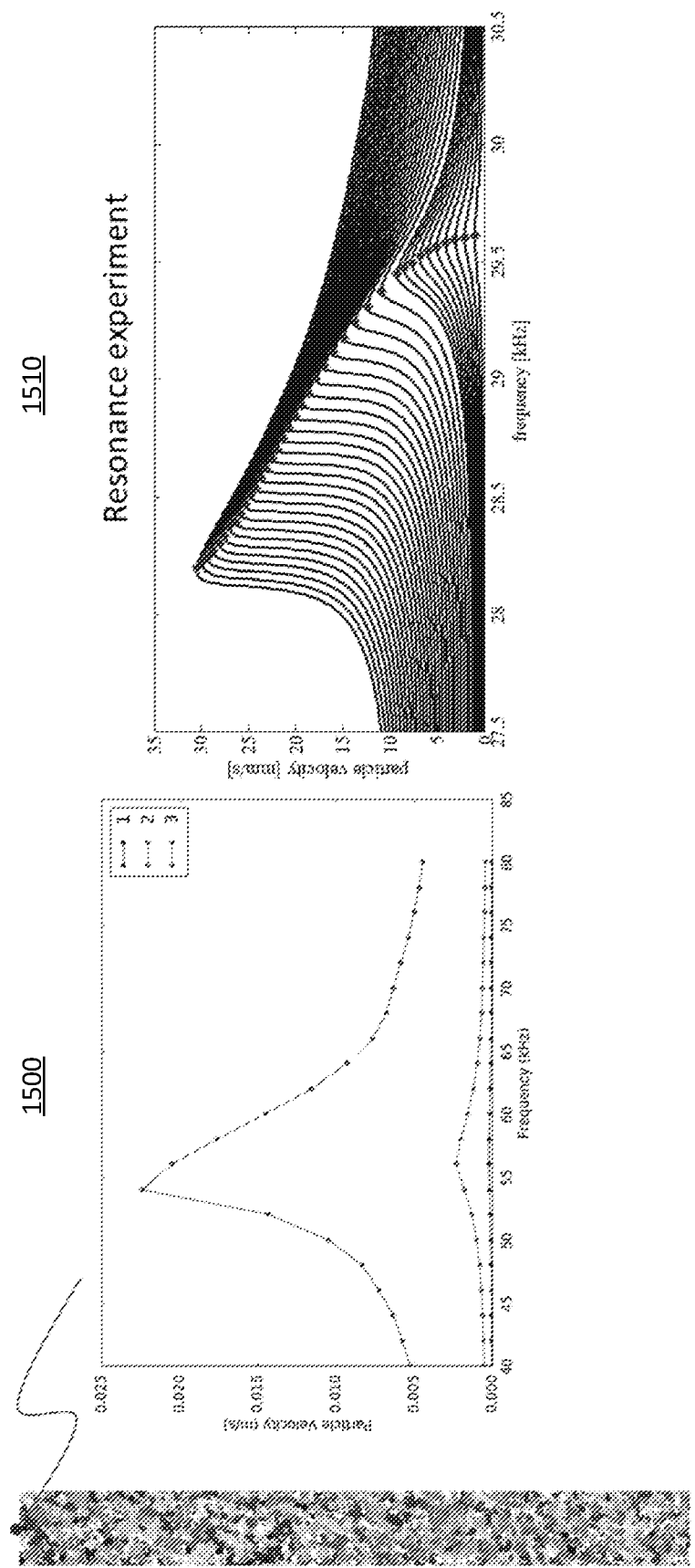
FIG. 15A illustrates an example comparison of a particle velocity-frequency graph obtained from simulation and a particle velocity-frequency graph obtained from resonance experiment.

FIG. 15A illustrates an example comparison of a particle velocity-frequency graph 1500 obtained from simulation and a particle velocity-frequency graph 1510 obtained from resonance experiment. The contact stiffness may be tuned to match the expected bulk properties of the system. The contact stiffness may be 40% of grain stiffness. The resonance curves obtained in a linear regime may indicate a resonance frequency at 56 kHz, compared to the 56 kHz frequency obtained with a simulation using a homogenous material (E=10 GPa). Similar relative shift of frequency $\Delta f/f0$ may be obtained between simulations and experiments.

Figure 15B:
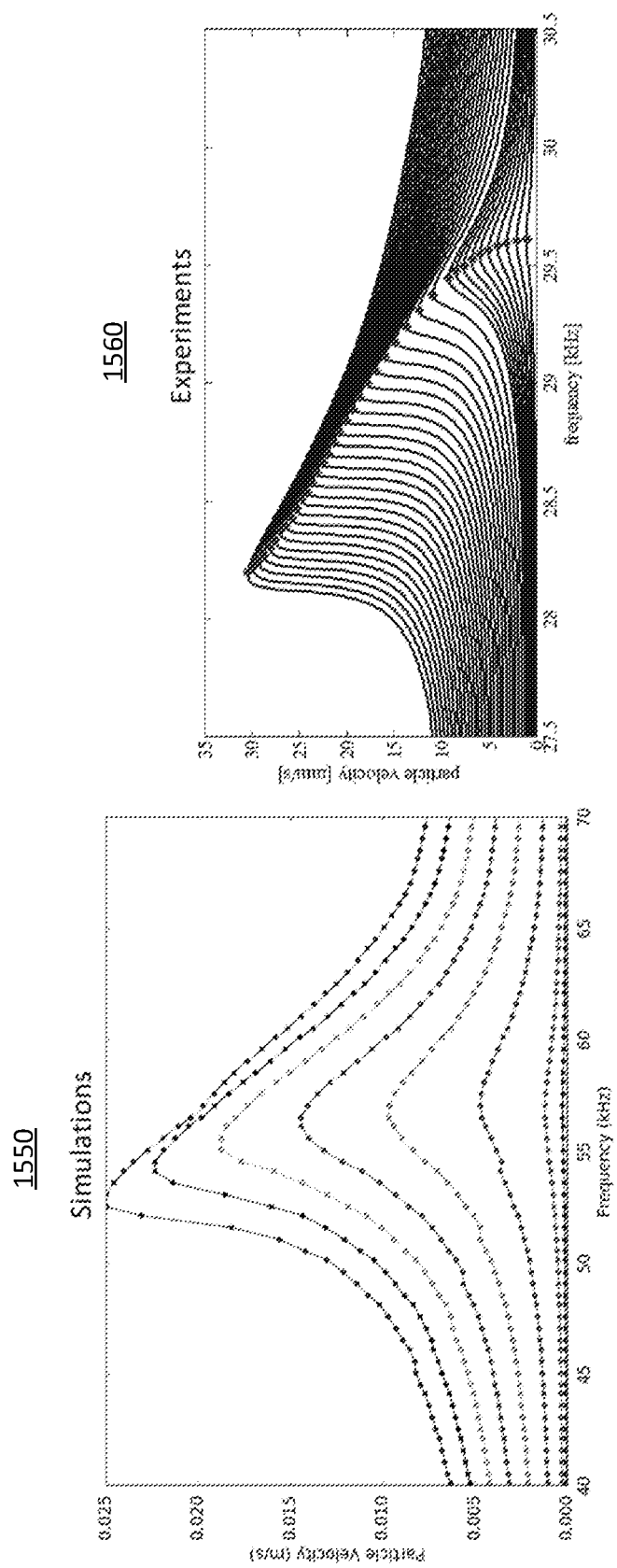
FIG. 15B illustrates an example comparison of a particle velocity-frequency graph obtained from simulation and a particle velocity-frequency graph obtained from resonance experiments.

FIG. 15B illustrates an example comparison of a particle velocity-frequency graph 1550 obtained from simulation and a particle velocity-frequency graph 1560 obtained from resonance experiments.

Figure 16:
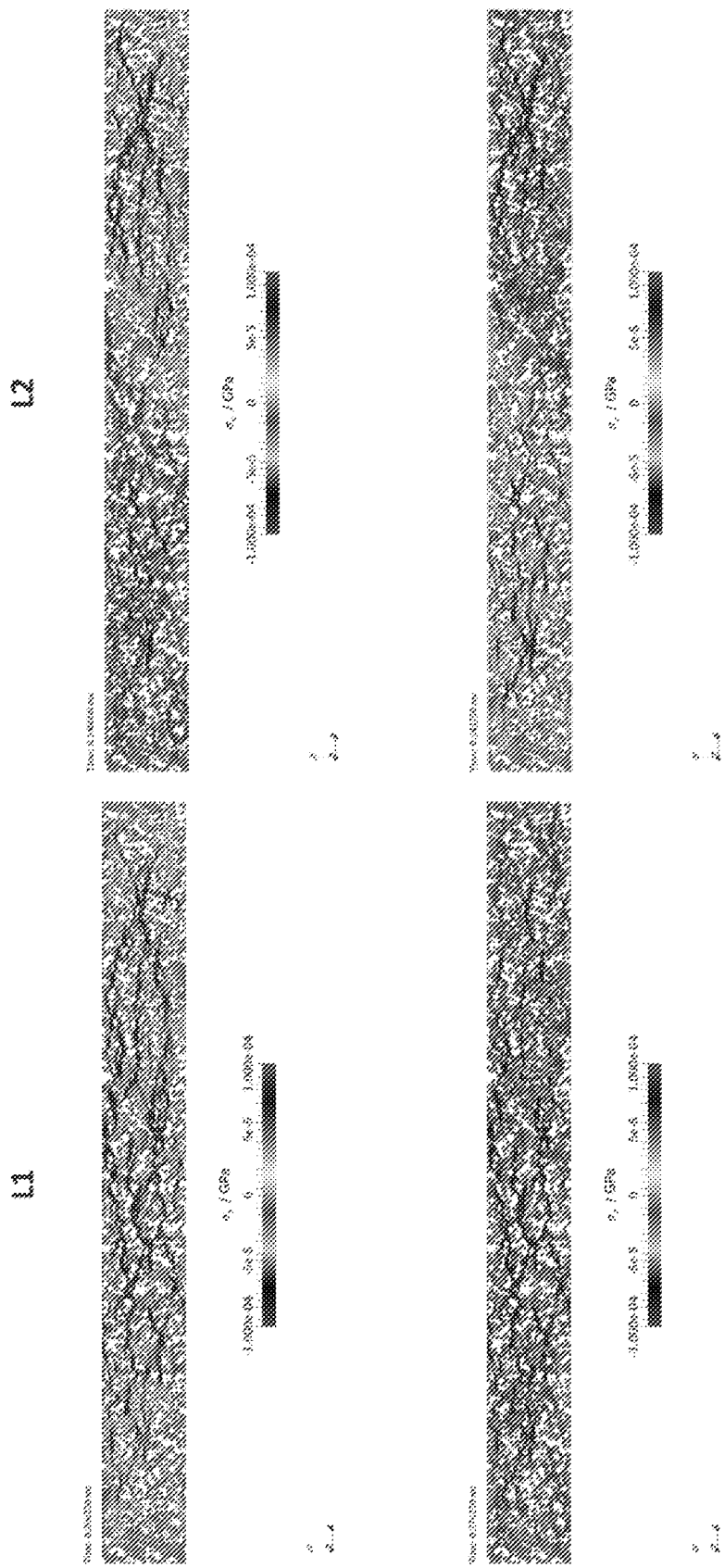
FIG. 16 illustrates example force chains within a model of a rock structure.

FIG. 16 illustrates example force chains within a model of a rock structure. L1 may illustrate snapshots of the force chains during a cycle of excitation at steady state for L1 (56 kHz). L2 may illustrate snapshots of the force chains during a cycle of excitation at steady state for L2 (112 kHz).

Figure 17:
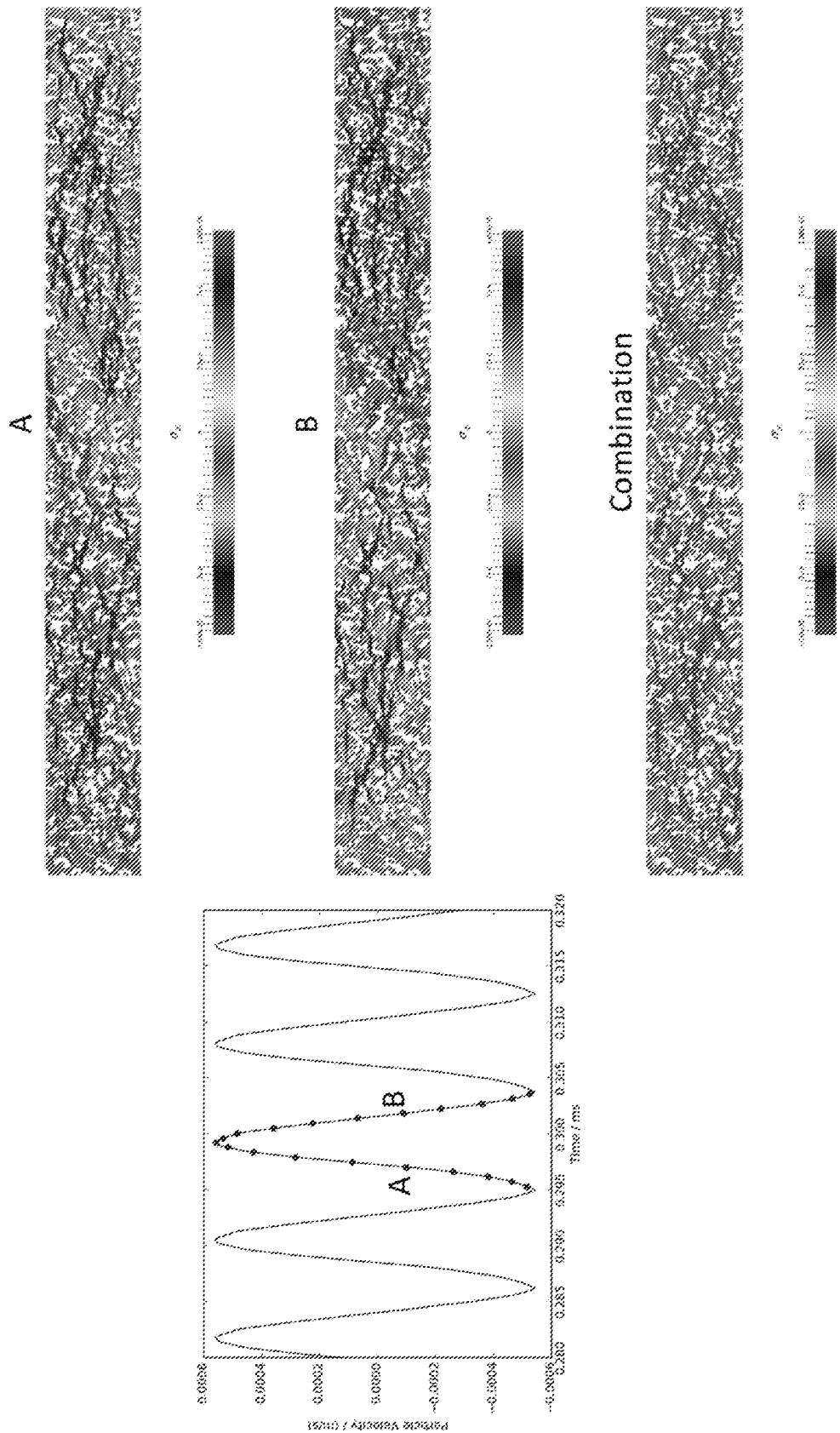
FIG. 17 illustrates an example combination of stress fields for force chains within a model of a rock structure.

FIG. 17 illustrates an example combination of stress fields for force chains within a model of a rock structure.

Figure 18:
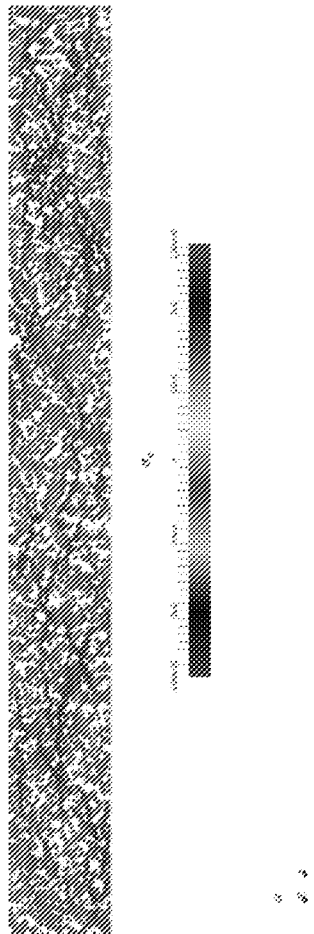
FIG. 18 illustrates example force chains within a model of a rock structure at different scales.
Figure 18:
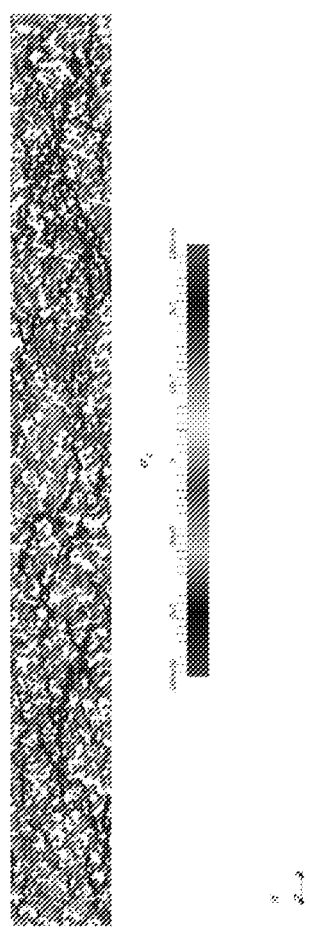

FIG. 18 illustrates example force chains within a model of a rock structure at different scales.

Figure 19:
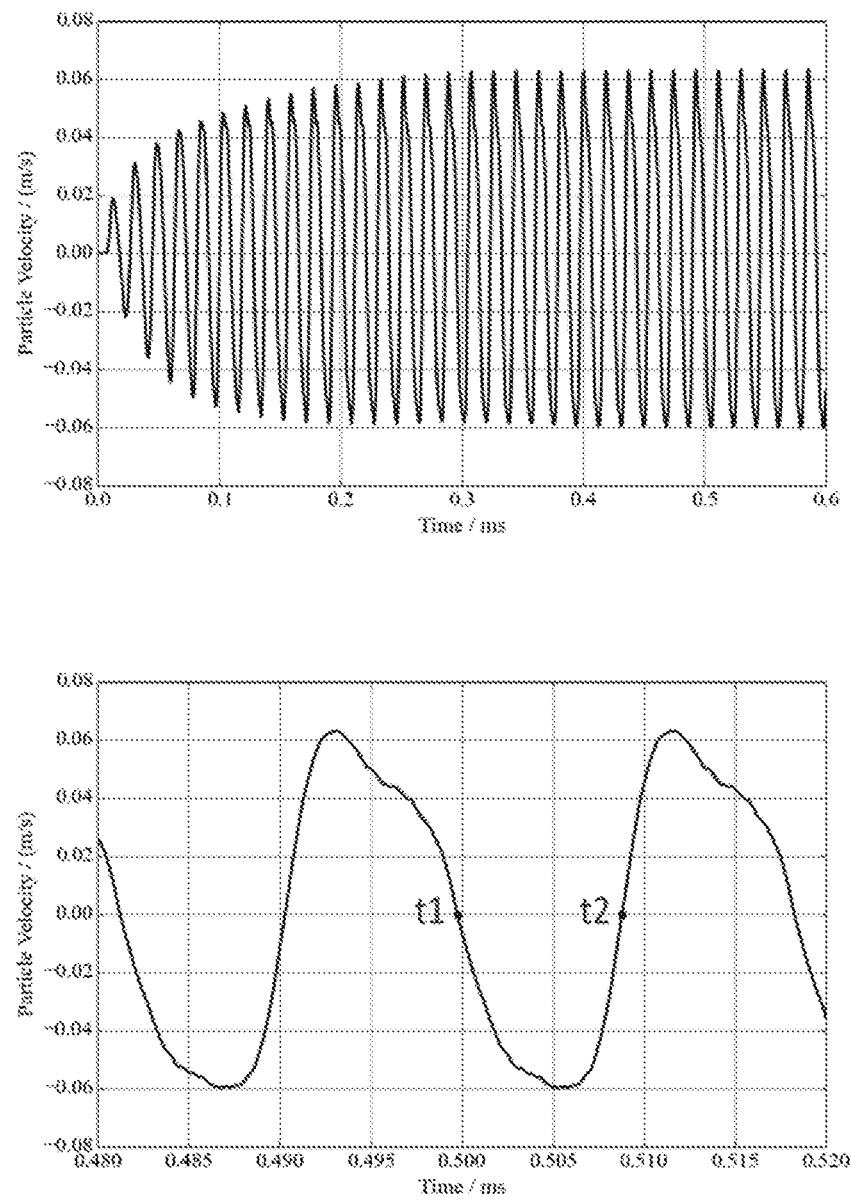
FIG. 19 illustrates example particle velocity graphs.
Figure 20:
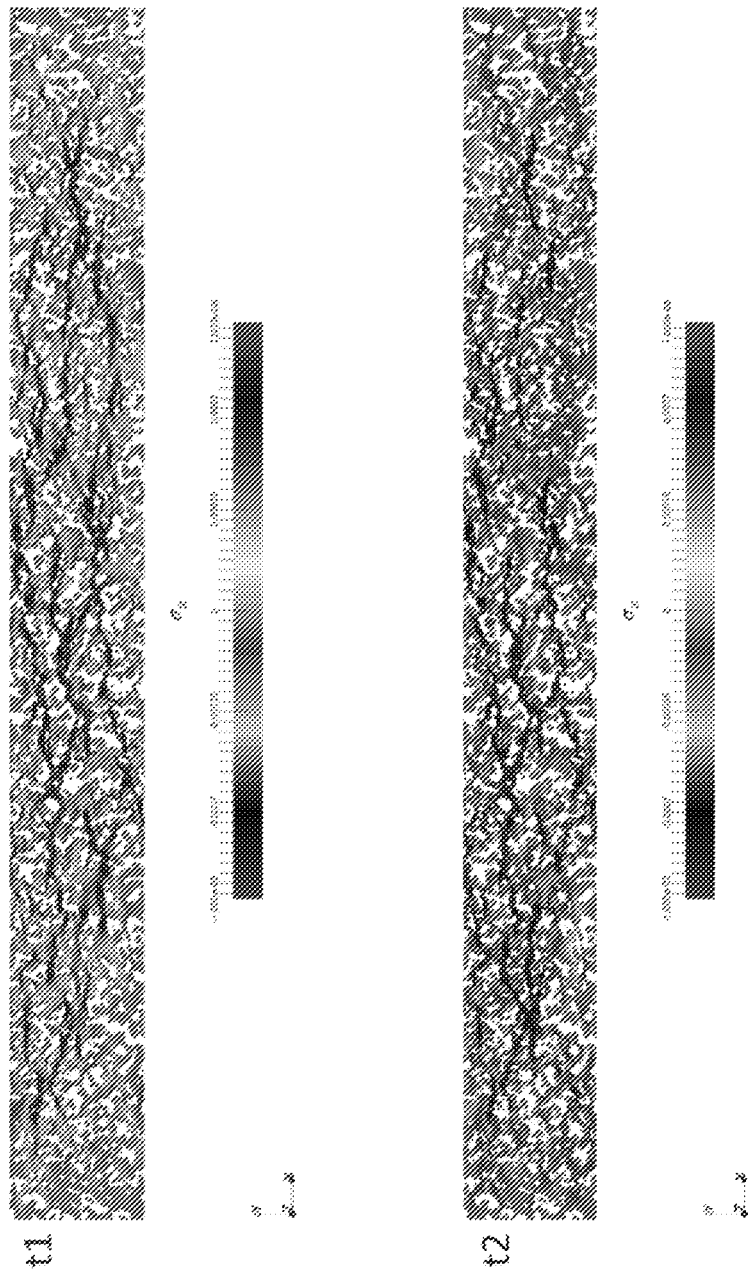
FIG. 20 illustrates example force chains within a model of a rock structure at times t1 and t2 of FIG. 19.

FIG. 19 illustrates example particle velocity graphs. FIG. 20 illustrates example force chains within a model of a rock structure at times t1 and t2 of FIG. 19.

The presentation component 106 may be configured to effectuate presentation of information on the characteristic(s) of the substance within the volume based on the structure model and/or other information. The information on the characteristic(s) of the substance within the volume may be presented on one or more displays. The display(s) may be local to the system 10 and/or remote from the system 10.

Information on the characteristic(s) of the substance within the volume may include information that quantifies, describes, and/or otherwise characterizes the characteristic(s) of the substance within the volume. For example, the presentation component 106 may effectuate presentation of values, descriptions, and/or representations (e.g., number representation, category representation, graph representation, image representation) of a pore pressure of a rock structure, a stress distribution within the rock structure, a force chain within the rock structure, a configuration of grains within the rock structure, a composition of the rock structure, a crack of the rock structure, a fracture of the rock structure, a fracture pattern of the rock structure, a fragmentation process of the rock structure, and/or other characteristics of the rock structure.

Information on the characteristic(s) of the substance within the volume may be used for analysis of the substance within the volume and/or to plan/perform one or more operations with respect to the substance within the volume. For example, the substance within the volume may include a rock structure, and information on the characteristic(s) of the rock structure may be analyzed to understand the nature of the rock structure. Information on the characteristic(s) of the rock structure may be used to plan usage of one or more drilling tools (device(s)/implement(s) designed and/or used for drilling into and/or through a substance (e.g., sedimentary rock)) on the rock structure. For instance, information on the characteristic(s) of the rock structure may be used to establish drilling parameters/parameter ranges for operating the drilling tool(s) on the rock structure. Other usage of the information on the characteristic(s) of the substance within the volume are contemplated.)

Additional descriptions of the present disclosure are found in Appendix A, Appendix B, Appendix C, Appendix D, and Appendix E of the '720 application.

Implementations of the disclosure may be made in hardware, firmware, software, or any suitable combination thereof. Aspects of the disclosure may be implemented as instructions stored on a machine-readable medium, which may be read and executed by one or more processors. A machine-readable medium may include any mechanism for storing or transmitting information in a form readable by a machine (e.g., a computing device). For example, a tangible (non-transitory) machine-readable storage medium may include read-only memory, random access memory, magnetic disk storage media, optical storage media, flash memory devices, and others, and a machine-readable transmission media may include forms of propagated signals, such as carrier waves, infrared signals, digital signals, and others. Firmware, software, routines, or instructions may be described herein in terms of specific exemplary aspects and implementations of the disclosure, and performing certain actions.

In some implementations, some or all of the functionalities attributed herein to the system 10 may be provided by external resources not included in the system 10. External resources may include hosts/sources of information, computing, and/or processing and/or other providers of information, computing, and/or processing outside of the system 10.

Although the processor 11 and the electronic storage 13 are shown to be connected to the interface 12 in FIG. 1, any communication medium may be used to facilitate interaction between any components of the system 10. One or more components of the system 10 may communicate with each other through hard-wired communication, wireless communication, or both. For example, one or more components of the system 10 may communicate with each other through a network. For example, the processor 11 may wirelessly communicate with the electronic storage 13. By way of non-limiting example, wireless communication may include one or more of radio communication, Bluetooth communication, Wi-Fi communication, cellular communication, infrared communication, or other wireless communication. Other types of communications are contemplated by the present disclosure.

Although the processor 11 is shown in FIG. 1 as a single entity, this is for illustrative purposes only. In some implementations, the processor 11 may comprise a plurality of processing units. These processing units may be physically located within the same device, or the processor 11 may represent processing functionality of a plurality of devices operating in coordination. The processor 11 may be separate from and/or be part of one or more components of the system 10. The processor 11 may be configured to execute one or more components by software; hardware; firmware; some combination of software, hardware, and/or firmware; and/or other mechanisms for configuring processing capabilities on the processor 11.

It should be appreciated that although computer program components are illustrated in FIG. 1 as being co-located within a single processing unit, in implementations in which processor 11 comprises multiple processing units, one or more of computer program components may be located remotely from the other computer program components. While computer program components are described as performing or being configured to perform operations, computer program components may comprise instructions which may program processor 11 and/or system 10 to perform the operation.

While computer program components are described herein as being implemented via processor 11 through machine-readable instructions 100, this is merely for ease of reference and is not meant to be limiting. In some implementations, one or more functions of computer program components described herein may be implemented via hardware (e.g., dedicated chip, field-programmable gate array) rather than software. One or more functions of computer program components described herein may be software-implemented, hardware-implemented, or software and hardware-implemented The description of the functionality provided by the different computer program components described herein is for illustrative purposes, and is not intended to be limiting, as any of computer program components may provide more or less functionality than is described. For example, one or more of computer program components may be eliminated, and some or all of its functionality may be provided by other computer program components. As another example, processor 11 may be configured to execute one or more additional computer program components that may perform some or all of the functionality attributed to one or more of computer program components described herein.

The electronic storage media of the electronic storage 13 may be provided integrally (i.e., substantially non-removable) with one or more components of the system 10 and/or removable storage that is connectable to one or more components of the system 10 via, for example, a port (e.g., a USB port, a Firewire port, etc.) or a drive (e.g., a disk drive, etc.). The electronic storage 13 may include one or more of optically readable storage media (e.g., optical disks, etc.), magnetically readable storage media (e.g., magnetic tape, magnetic hard drive, floppy drive, etc.), electrical charge-based storage media (e.g., EPROM, EEPROM, RAM, etc.), solid-state storage media (e.g., flash drive, etc.), and/or other electronically readable storage media. The electronic storage 13 may be a separate component within the system 10, or the electronic storage 13 may be provided integrally with one or more other components of the system 10 (e.g., the processor 11). Although the electronic storage 13 is shown in FIG. 1 as a single entity, this is for illustrative purposes only. In some implementations, the electronic storage 13 may comprise a plurality of storage units. These storage units may be physically located within the same device, or the electronic storage 13 may represent storage functionality of a plurality of devices operating in coordination.

Figure 2:
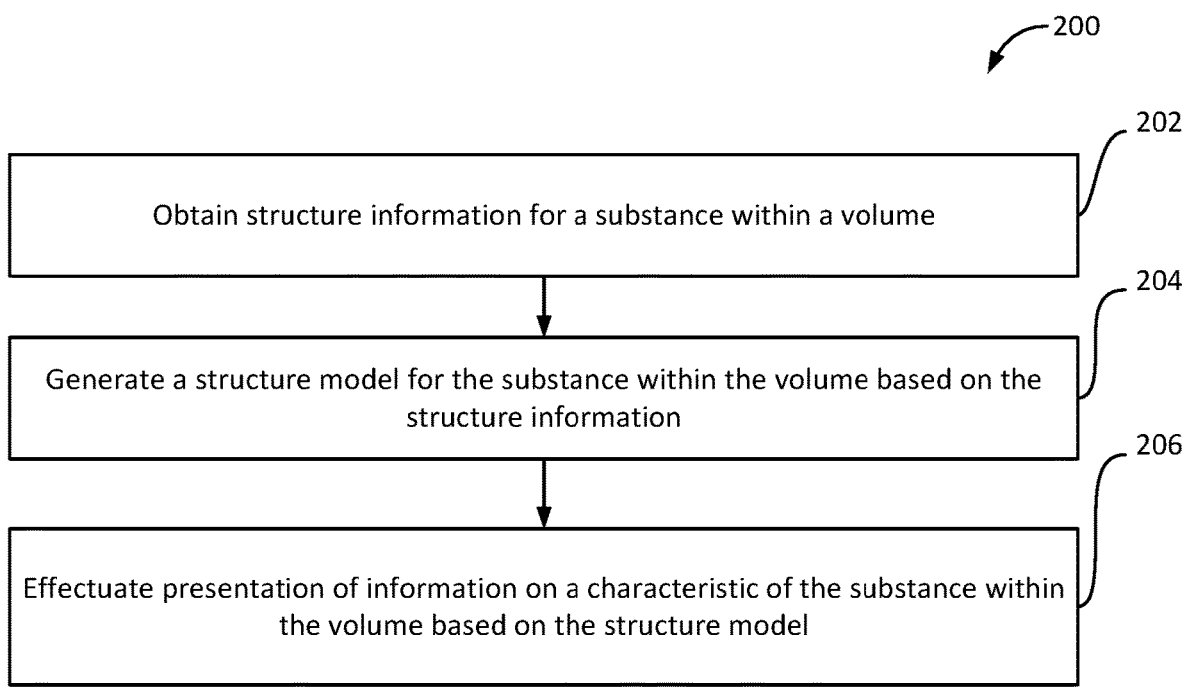
FIG. 2 illustrates an example method for modeling substance characteristics based on structural non-linearity of a substance.

FIG. 2 illustrates method 200 for modeling substance characteristics based on structural non-linearity of a substance. The operations of method 200 presented below are intended to be illustrative. In some implementations, method 200 may be accomplished with one or more additional operations not described, and/or without one or more of the operations discussed. In some implementations, two or more of the operations may occur substantially simultaneously.

In some implementations, method 200 may be implemented in one or more processing devices (e.g., a digital processor, an analog processor, a digital circuit designed to process information, a central processing unit, a graphics processing unit, a microcontroller, an analog circuit designed to process information, a state machine, and/or other mechanisms for electronically processing information). The one or more processing devices may include one or more devices executing some or all of the operations of method 200 in response to instructions stored electronically on one or more electronic storage mediums. The one or more processing devices may include one or more devices configured through hardware, firmware, and/or software to be specifically designed for execution of one or more of the operations of method 200.

Referring to FIG. 2 and method 200, at operation 202, structure information for a substance within a volume may be obtained. The structure information may characterize structural non-linearity of the substance within the volume. In some implementation, operation 202 may be performed by a processor component the same as or similar to the structure information component 102 (Shown in FIG. 1 and described herein).

At operation 204, a structure model for the substance within the volume may be generated based on the structure information. The structure model may simulate a characteristic of the substance within the volume. In some implementation, operation 204 may be performed by a processor component the same as or similar to the structure model component 104 (Shown in FIG. 1 and described herein).

At operation 206, presentation of information on the characteristic of the substance within the volume may be effectuated based on the structure model. In some implementation, operation 206 may be performed by a processor component the same as or similar to the presentation component 106 (Shown in FIG. 1 and described herein).

Although the system(s) and/or method(s) of this disclosure have been described in detail for the purpose of illustration based on what is currently considered to be the most practical and preferred implementations, it is to be understood that such detail is solely for that purpose and that the disclosure is not limited to the disclosed implementations, but, on the contrary, is intended to cover modifications and equivalent arrangements that are within the spirit and scope of the appended claims. For example, it is to be understood that the present disclosure contemplates that, to the extent possible, one or more features of any implementation can be combined with one or more features of any other implementation.

What is claimed is:

1. A system for modeling substance characteristics, the system comprising:
   a sensor configured to receive an acoustic wave that travels through a substance within a volume;
   a display; and
   one or more physical processors configured by machine-readable instructions to:
      determine resonance frequencies of the substance within the volume based on the received acoustic wave;
      select a resonance frequency from the resonance frequencies;
      generate a resonance frequency acoustic wave for transmission through the substance within the volume multiple times, the resonance frequency acoustic wave having the selected resonance frequency and having different amplitudes for individual ones of the multiple times;
      determine changes in the resonance frequencies of the substance within the volume as a function of the different amplitudes of the resonance frequency acoustic wave; and determine structural non-linearity of the substance within the volume based on the changes in the resonance frequencies of the substance within the volume as the function of the different amplitudes of the resonance frequency acoustic wave;

generate a structure model for the substance within the volume based on the structural non-linearity of the substance within the volume, the generation of the structure model based on the structure non-linearity of the substance within the volume enabling component-scale modeling of the substance within the volume;

simulate a characteristic of the substance within the volume using the structure model; and effectuate presentation, on the display, of information on the simulated characteristic of the substance within the volume.

2. The system of claim 1, wherein the substance within the volume includes a rock structure.

3. The system of claim 2, wherein the characteristic of the substance within the volume includes one or more of a pore pressure of the rock structure, a stress distribution within the rock structure, a force chain within the rock structure, a configuration of grains within the rock structure, a composition of the rock structure, a crack of the rock structure, a fracture of the rock structure, a fracture pattern of the rock structure, and/or a fragmentation process of the rock structure.

4. The system of claim 2, wherein the changes in the resonance frequencies of the substance within the volume as the function of the different amplitudes of the resonance frequency acoustic wave indicate a change in stiffness of the rock structure.

5. The system of claim 2, wherein the characteristic of the substance within the volume is simulated by the structure model based on a grain-scale modeling that takes into account non-uniform structure of grains within the rock structure.

6. The system of claim 1, wherein usage of a drilling tool to drill into and/or through the substance within the volume is planned based on the simulated characteristic of the substance within the volume.

7. The system of claim 1, wherein drilling parameters or drilling parameter ranges for operating a drilling tool on the substance within the volume are determined based on the simulated characteristic of the substance within the volume.

8. A method for modeling substance characteristics, the method performed by a system including a sensor, a display, and one or more processors, the sensor configured to receive an acoustic wave that travels through a substance within a volume, the method comprising:

determining resonance frequencies of the substance within the volume based on the received acoustic wave;

selecting a resonance frequency from the resonance frequencies;

generating a resonance frequency acoustic wave for transmission through the substance within the volume multiple times, the resonance frequency acoustic wave having the selected resonance frequency and having different amplitudes for individual ones of the multiple times;

determining changes in the resonance frequencies of the substance within the volume as a function of the different amplitudes of the resonance frequency acoustic wave; and determining structural non-linearity of the substance within the volume based on the changes in the resonance frequencies of the substance within the volume as the function of the different amplitudes of the resonance frequency acoustic wave;

generating a structure model for the substance within the volume based on the structural non-linearity of the substance within the volume, the generation of the structure model based on the structure non-linearity of the substance within the volume enabling component-scale modeling of the substance within the volume;

simulating a characteristic of the substance within the volume using the structure model; and effectuating presentation, on the display, of information on the simulated characteristic of the substance within the volume.

9. The method of claim 8, wherein the substance within the volume includes a rock structure.

10. The method of claim 9, wherein the characteristic of the substance within the volume includes one or more of a pore pressure of the rock structure, a stress distribution within the rock structure, a force chain within the rock structure, a configuration of grains within the rock structure, a composition of the rock structure, a crack of the rock structure, a fracture of the rock structure, a fracture pattern of the rock structure, and/or a fragmentation process of the rock structure.

11. The method of claim 9, wherein the changes in the resonance frequencies of the substance within the volume as the function of the different amplitudes of the resonance frequency acoustic wave indicate a change in stiffness of the rock structure.

12. The method of claim 9, wherein the characteristic of the substance within the volume is simulated by the structure model based on a grain-scale modeling that takes into account non-uniform structure of grains within the rock structure.

13. The method of claim 8, wherein usage of a drilling tool to drill into and/or through the substance within the volume is planned based on the simulated characteristic of the substance within the volume.

14. The method of claim 8, wherein drilling parameters or drilling parameter ranges for operating a drilling tool on the substance within the volume are determined based on the simulated characteristic of the substance within the volume.

* * * * *